(12) United States Patent
Chen et al.

(10) Patent No.: US 11,066,384 B2
(45) Date of Patent: Jul. 20, 2021

(54) CRYSTALLINE FORMS OF ARN-509, PREPARATION METHOD AND USE THEREOF

(71) Applicant: Crystal Pharmaceutical (Suzhou) Co., Ltd., Suzhou (CN)

(72) Inventors: Minhua Chen, Suzhou (CN); Yanfeng Zhang, Suzhou (CN); Xiaoting Zhai, Suzhou (CN); Jiale Qian, Suzhou (CN); Yuhao Chen, Suzhou (CN); Chaohui Yang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 17/033,922

(22) Filed: Sep. 28, 2020

(65) Prior Publication Data

US 2021/0017148 A1    Jan. 21, 2021

Related U.S. Application Data

(63) Continuation of application No. 16/763,554, filed as application No. PCT/CN2019/087264 on May 16, 2019, now abandoned.

(30) Foreign Application Priority Data

Jun. 20, 2018 (CN) .......................... 201810639839.8
Jun. 20, 2018 (CN) .......................... 201810639840.0

(51) Int. Cl.
C07D 401/04    (2006.01)

(52) U.S. Cl.
CPC ........ C07D 401/04 (2013.01); C07B 2200/13 (2013.01)

(58) Field of Classification Search
CPC .................................................. C07D 401/04
USPC ........................................................ 514/339
See application file for complete search history.

(56) References Cited

U.S. PATENT DOCUMENTS

| | | | |
|---|---|---|---|
| 8,445,507 B2 | 5/2013 | Jung et al. | |
| 9,481,663 B2 * | 11/2016 | Dilhas .................. | A61P 5/28 |
| 10,308,630 B2 | 6/2019 | Dilhas et al. | |
| 2019/0322640 A1 | 10/2019 | Muthusamy et al. | |
| 2020/0270226 A1 | 8/2020 | Chen et al. | |

FOREIGN PATENT DOCUMENTS

| | | | |
|---|---|---|---|
| CN | 104619692 A | 5/2015 | |
| CN | 105732575 A | 7/2016 | |
| WO | 2008/119015 A2 | 10/2008 | |
| WO | WO-2013184681 A1 * | 12/2013 | ................ A61P 5/28 |

OTHER PUBLICATIONS

International Search Report and Written Opinion for Application No. PCT/CN2019/087264, dated Aug. 16, 2019, 12 pages.
U.S. Appl. No. 16/763,554, filed May 13, 2020, 2020-0270226, Published.
Supplementary European Search Report for Application No. 19821984.2, dated Mar. 18, 2021, 8 pages.

* cited by examiner

*Primary Examiner* — Kahsay Habte
(74) *Attorney, Agent, or Firm* — McCarter & English, LLP; Wei Song

(57) ABSTRACT

The present disclosure relates to novel crystalline forms of ARN-509 (structure shown in formula I), processes for preparation of the novel crystalline forms, pharmaceutical composition of the novel crystalline forms, and uses of the novel crystalline forms for preparing drug products of androgen receptor antagonists and for treating prostate cancer. The crystalline forms of ARN-509 provided by the present disclosure have one or more improved properties compared with the prior art, and is of great value to the future optimization and development of drugs.

Formula (I)

18 Claims, 25 Drawing Sheets

CRYSTALLINE FORMS OF ARN-509, PREPARATION METHOD AND USE THEREOF

CROSS-REFERENCE TO RELATED APPLICATIONS

This application is a continuation of U.S. patent application Ser. No. 16/763,554, filed on May 13, 2020, which is a U.S. national stage filing, under 35 U.S.C. § 371(c), of International Application No. PCT/CN2019/087264, filed on May 16, 2019, which claims priority to Chinese Patent Application No. 201810639839.8, filed on Jun. 20, 2018, and Chinese Patent Application No. 201810639840.0, filed on Jun. 20, 2018. The entire contents of each of the aforementioned applications are incorporated herein by reference.

TECHNICAL FIELD

The present disclosure relates to the field of pharmaceutical chemistry, particularly relates to novel crystalline forms of ARN-509, processes for preparation and use thereof.

BACKGROUND

Prostate cancer is the cancer with highest incidence and second highest mortality rate in men. Data from the American Cancer Society show that there were approximately 180,000 new cases in the United States in 2016, and about 3 million patients with prostate cancer. In 1941, Huggins and Hodges first demonstrated the response of prostate cancer to androgen removal. Therapies that inhibit androgen activity have been widely used in the treatment of prostate cancer.

Abiraterone and Enzalutamide are the first-generation androgen receptor antagonists and have been approved for the treatment of prostate cancer. In clinical trials, it is effective in about 70% of patients. The response rate is much higher than the drugs targeting other targets, which further proves the importance of androgens for the treatment of prostate cancer.

ARN-509 (Apalutamide) is a second-generation androgen receptor antagonist used for the treatment of prostate cancer in the clinical research. It prevents androgen from binding to androgen receptor by binding with the androgen receptor, thereby inhibiting the androgen receptor signaling pathway and achieving the purpose of treating prostate cancer. ARN-509 has shown positive safety and efficacy in clinic trials, and shows good therapeutic prospect.

The chemical name of ARN-509 is 4-[7-(6-cyano-5-trifluoromethylpyridin-3-yl)-8-oxo-6-thioxo-5,7-diazaspiro[3.4]oct-5-yl]-2-fluoro-N-methylbenzamide, and the structure is shown as Formula I:

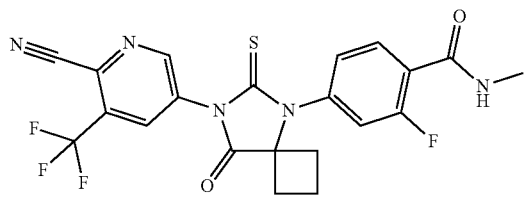

Formula I

A crystalline form is a solid material whose constituents are arranged in a highly ordered microscopic structure, forming a crystal lattice that extends in all directions. Polymorphism is the ability of a compound to exist in more than one crystalline form. Different crystalline forms have different physicochemical properties and can affect drug's in vivo dissolution and absorption, which will further affect drug's clinical efficacy and safety to some extent. Especially for poorly soluble drugs, the above effects of the crystalline form will be greater. Therefore, drug polymorphism is an important part of drug research and an important part of drug quality control.

The prior art WO2013184681A disclosed crystalline form A, form B, form C, form D, form E, form F, form G, form H, form I and form J of ARN-509. Among them, form C is an isopropanol solvate, form D is a methyl tert-butyl ether solvate, form E is a dimethyl sulfoxide solvate, form G is a 2-methoxyethanol solvent, and form J is an acetone solvate. Therefore, form C, form D, form E, form G and form J are not suitable for pharmaceutical use. Form F will transform to form A under ambient conditions. During the process of preparation of form I, form E will be formed and it is difficult to separate them. Form I will transform to form B under high humidity conditions. Form H is easily transformed into form B under high temperature and high humidity conditions. It can be seen that form F, form H, and form I are not suitable for industrial production and application. According to WO2013184681A, the preferred crystalline form that may be suitable for pharmaceutical use are form A and form B. The inventors of the present disclosure discovered that the solubility, in vitro dissolution, grinding stability, adhesion and compressibility of the prior art form A and form B are poor, which is not conducive to the in vivo absorption of drugs and industrial production of drug products.

In order to overcome the disadvantages of the prior art, the inventors of the present disclosure surprisingly discovered crystalline form CS8 and form CS9 of ARN-509, which have advantages in physiochemical properties, formulation processability and bioavailability. For example, crystalline form CS8 and form CS9 have advantages in at least one aspect of melting point, solubility, hygroscopicity, purification ability, stability, adhesiveness, compressibility, flowability, in vitro and in vivo dissolution, and bioavailability, etc. Particularly, crystalline form CS8 and form CS9 have higher solubility and in vitro dissolution, better stability, uniform particle size distribution, better adhesion and compressibility, which provides a new and better choice for the development of ARN-509 and is of great significance for drug development.

SUMMARY

The main objective of the present disclosure is to provide novel crystalline forms of ARN-509, processes for preparation and use thereof.

According to the objective of the present disclosure, crystalline form CS8 of ARN-509 is provided (hereinafter referred to as Form CS8).

The X-ray powder diffraction pattern of Form CS8 shows characteristic peaks at 2theta values of 7.9±0.2°, 12.4±0.2° and 19.0±0.2° using CuKα radiation.

Furthermore, the X-ray powder diffraction pattern of Form CS8 shows one or two or three characteristic peaks at 2theta values of 15.4±0.2°, 19.6±0.2° and 22.5±0.2°. Preferably, the X-ray powder diffraction pattern of Form CS8 shows characteristic peaks at 2theta values of 15.4±0.2°, 19.6±0.2° and 22.5±0.2°.

Furthermore, the X-ray powder diffraction pattern of Form CS8 shows one or two or three characteristic peaks at 2theta values of 23.2±0.2°, 16.0±0.2° and 24.0±0.2°. Preferably, the X-ray powder diffraction pattern of Form CS8 shows characteristic peaks at 2theta values of 23.2±0.2°, 16.0±0.2° and 24.0±0.2°.

The X-ray powder diffraction pattern of Form CS8 shows three or four or five or six or seven or eight or nine characteristic peaks at 2theta values of 7.9±0.2°, 12.4±0.2°, 19.0±0.2°, 15.4±0.2°, 19.6±0.2°, 22.5±0.2°, 23.2±0.2°, 16.0±0.2° and 24.0±0.2° using CuKα radiation.

Without any limitation being implied, in a specific embodiment of the present disclosure, the X-ray powder diffraction pattern of Form CS8 is substantially as depicted in FIG. 1.

Without any limitation being implied, in some embodiments of the present disclosure, Form CS8 is a hydrate.

According to the objective of the present disclosure, a process for preparing Form CS8 is also provided. The process comprises:

(1) Dissolving ARN-509 into a solvent of alcohols, cooling to −20° C.-16° C., precipitating solid to obtain Form CS8; or (2) Dissolving ARN-509 into ethyl formate, cooling to −20° C.-10° C., and drying the obtain solid under vacuum at 5° C.-70° C. to obtain Form CS8; or (3) Dissolving ARN-509 into a solvent mixture of methyl acetate, alcohols and alkanes, stirring at 0° C.-10° C., separating by filtration, and drying the obtained solid with forced air convection at 20° C.-40° C. to obtain Form CS8.

Furthermore, in method (1), said alcohol is preferably methanol; said cooling temperature is preferably 10° C.;

Furthermore, in method (2), said cooling temperature is preferably −5° C.; said vacuum-drying temperature is preferably 60° C.;

Furthermore, in method (3), said alcohol is preferably methanol, said alkane is preferably cyclohexane, said stirring temperature is preferably 5° C., said drying with forced air convection temperature is preferably 30° C.

According to the objective of the present disclosure, crystalline form CS9 of ARN-509 is provided (hereinafter referred to as Form CS9).

The X-ray powder diffraction pattern of Form CS9 shows characteristic peaks at 2theta values of 7.7±0.2°, 15.0±0.2° and 18.0±0.2° using CuKα radiation.

Furthermore, the X-ray powder diffraction pattern of Form CS9 shows one or two or three characteristic peaks at 2theta values of 12.3±0.2°, 19.9±0.2° and 20.7±0.2°. Preferably, the X-ray powder diffraction pattern of Form CS9 shows characteristic peaks at 2theta values of 12.3±0.2°, 19.9±0.2° and 20.7±0.2°.

Furthermore, the X-ray powder diffraction pattern of Form CS9 shows one or two or three characteristic peaks at 2theta values of 15.5±0.2°, 22.6±0.2° and 23.0±0.2°. Preferably, the X-ray powder diffraction pattern of Form CS9 shows characteristic peaks at 2theta values of 15.5±0.2°, 22.6±0.2° and 23.0±0.2°.

The X-ray powder diffraction pattern of Form CS9 shows three or four or five or six or seven or eight or nine characteristic peaks at 2theta values of 7.7±0.2°, 15.0±0.2°, 18.0±0.2°, 12.3±0.2°, 19.9±0.2°, 20.7±0.2°, 15.5±0.2°, 22.6±0.2° and 23.0±0.2° using CuKα radiation.

Without any limitation being implied, in a specific embodiment of the present disclosure, the X-ray powder diffraction pattern of Form CS9 is substantially as depicted in FIG. 7.

Without any limitation being implied, Form CS9 can be obtained in different solvent systems and represents a group of isomorphism. In some embodiments, Form CS9 is an acetonitrile solvate. In some embodiments, Form CS9 can also be methyl acetate solvate or co-solvate of methyl acetate and water.

Without any limitation being implied, in a specific embodiment of the present disclosure, Form CS9 is a co-solvate of methyl acetate and water. The parameters of the single crystal structure are shown in the following table:

| Crystal system | Orthogonal | | |
|---|---|---|---|
| Space group | $Pna2_1$ | | |
| Unit cell dimensions | a   9.1489(11) Å | α | 90.00° |
| | b   16.077(2) Å | β | 90.00° |
| | c   16.817(2) Å | γ | 90.00° |
| Volume of unit cell (V) | 2473.6(5) Å$^3$ | | |
| Number of formula units in unit cell (Z) | 4 | | |
| Calculated density | 1.395 g/cm$^3$ | | |

Without any limitation being implied, in another specific embodiment of the present disclosure, Form CS9 is an acetonitrile solvate. The parameters of the single crystal structure are shown in the following table:

| Crystal system | Orthogonal | | |
|---|---|---|---|
| Space group | $Pna2_1$ | | |
| Unit cell dimensions | a   9.0288(15) Å | α | 90.00° |
| | b   15.295(2) Å | β | 90.00° |
| | c   16.948(3) Å | γ | 90.00° |
| Volume of unit cell (V) | 2340.5(6) Å$^3$ | | |
| Number of formula units in unit cell (Z) | 4 | | |
| Calculated density | 1.471 g/cm$^3$ | | |

According to the objective of the present disclosure, a process for preparing Form CS9 is also provided. The process comprises:

(1) Adding ARN-509 into nitriles, the mixture of nitriles and water, the mixture of nitriles and alcohols, or the mixture of nitriles and aromatic hydrocarbons, stirring at 5° C.-50° C., centrifuging and drying to obtain solid, or (2) Dissolving ARN-509 into a solvent mixture of methyl acetate, alcohols and alkanes, heating to 40° C.-60° C., and then cooling to 0° C.-10° C. to precipitate solid; or (3) Dissolving ARN-509 into a solvent mixture of acetonitrile and alcohols, cooling to −20° C.-5° C. to precipitate solid.

Furthermore, in method (1), said nitrile is preferably acetonitrile, said alcohol is preferably methanol or ethanol, said aromatic hydrocarbon is preferably toluene;

Furthermore, in method (1), said stirring temperature is preferably room temperature or 50° C.;

Furthermore, in method (2), said alcohol is preferably methanol, said alkane is preferably n-heptane;

Furthermore, in method (2), said heating temperature is preferably 50° C., said cooling temperature is preferably 5° C.;

Furthermore, in method (3), said alcohol is preferably isopropanol;

Furthermore, in method (3), said cooling temperature is preferably −20° C.

Form CS8 of the present disclosure has the following advantages:

(1) Compared with the prior art, Form CS8 of the present disclosure has higher solubility. In pH=1.0 HCl aqueous solution, after equilibrated for 15 minutes, the solubility of Form CS8 is 3.2 times higher than that of Form A of the prior art and 19.7 times higher than that of Form B of the prior art.

In pH=4.5 acetic acid buffer solution, after equilibrated for 15 minutes, the solubility of Form CS8 is 3.0 times higher than that of Form A and 16.1 times higher than that of Form B of the prior art. In pH=6.8 phosphate buffer solution, after equilibrated for 15 minutes, the solubility of Form CS8 is 3.7 times higher than that of Form A of the prior art and 19.0 times higher than that of Form B of the prior art.

ARN-509 is a poorly water-soluble drug and belongs to BCS II (low solubility and high permeability). Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(2) Compared with the prior art, Form CS8 of the present disclosure has better in vitro dissolution and dissolution rate. In pH=4.5 acetic acid buffer solution+0.5% (W/W) sodium dodecyl sulfate aqueous solution, the dissolution of Form CS8 drug products is up to 81% at 60 minutes. However, the dissolution of Form A and Form B of the prior art drug products are only 44% and 66%, respectively.

Drug with different crystalline forms may lead to different in vivo dissolution rate, which directly affects drug's in vivo absorption, distribution, excretion and metabolism, and finally leads to difference in clinical efficacy due to different bioavailability. Dissolution and dissolution rates are important prerequisites for drug absorption. Good in vitro dissolution is conducive to increasing the degree of drug absorption and ensuring better in vivo exposure, thereby improving drug's bioavailability and efficacy. High dissolution rate is beneficial for the drug to achieve peak concentration in plasma quickly after administration, thus ensuring rapid drug action.

(3) Form CS8 drug substance of the present disclosure has good stability and it also has good stability in drug products.

Form CS8 drug substance doesn't change for at least 6 months when stored under the condition of 25° C./60% RH. The chemical purity is above 99.9% and remains substantially unchanged during storage. Form CS8 is blended with the excipients to form drug products, and stored under the condition of 25° C./60% RH, the Form CS8 drug products doesn't change for at least 3 months. The chemical purity remains substantially unchanged during storage. These results show that Form CS8 drug substance of the present disclosure is very stable and it has good stability in drug products, which is beneficial for the storage of drug products.

Meanwhile, Form CS8 drug substance doesn't change for at least 6 months when stored under the condition of 40° C./75% RH. The chemical purity is above 99.9% and remains substantially unchanged during storage. Form CS8 is blended with the excipients to form drug products, and stored under the condition of 40° C./75% RH, the Form CS8 drug products doesn't change for at least 3 months. The chemical purity remains substantially unchanged during storage. Furthermore, Form CS8 doesn't change for at least 2 weeks when stored under the condition of 60° C./75% RH. The results show that Form CS8 drug substance and drug products have better stability under accelerated and stress conditions. Good stability of drug substance and drug products under accelerated and stress conditions is of great importance to the drug development. Drug substance and drug products will go through high temperature and high humidity conditions caused by seasonal and regional climate differences, and weather factors during storage, transportation, and manufacturing processes. Form CS8 drug substance and drug products have good stability under these stress conditions, which is beneficial to avoid the influence on drug quality when not stored in condition recommended in label.

Meanwhile, compared with the prior art, Form CS8 has better mechanical stability. The crystalline form and crystallinity of Form CS8 doesn't change after grinding. While Form A of the prior art transformed into amorphous after grinding and the crystallinity of Form B of the prior art decreases after grinding. Grinding and pulverization are often required in the drug manufacturing process. Good physical stability of the drug substance can reduce the risk of crystallinity decrease and crystal transformation during the drug production process. Meanwhile, Form CS8 has good physical stability under different pressure, which is beneficial to keep crystalline form unchanged during tableting process.

Crystal transformation and crystallinity decrease can lead to changes in the absorption of the drug, affect bioavailability, and even cause toxicity and side effects. Good chemical stability ensures that no impurities are generated during storage. Form CS8 has good physical and chemical stability, ensuring consistent and controllable quality of the drug substance and drug products, minimizing change in quality, bioavailability due to crystal transformation or impurity generation.

Furthermore, Form CS8 of the present disclosure also has the following advantages:

(1) Compared with the prior art, Form CS8 of the present disclosure has uniform particle size distribution. Its uniform particle size helps to ensure uniformity of content and reduce variability of in vitro dissolution. Meanwhile, the preparation process can be simplified, the pretreatment of the drug substance is not required, the cost is reduced, and the risk of decrease in crystallinity and crystal transformation caused by grinding can be reduced.

(2) Compared with the prior art, Form CS8 of the present disclosure shows superior adhesiveness. Adhesiveness evaluation results indicate that adhesion quantity of Form CS8 is remarkably lower than that of the prior art forms. Due to superior adhesiveness of Form CS8, adhesion to roller and tooling during dry-granulation and compression process can be reduced, which is also beneficial to improve product appearance and weight variation. In addition, superior adhesiveness of Form CS8 can reduce the agglomeration of drug substance, which is beneficial to the dispersion of drug substance and blending with other excipients, improving the blend uniformity and content uniformity of drug products.

(3) Compared with the prior art, Form CS8 of the present disclosure has better compressibility. Failure in hardness/friability test and tablet crack issue can be avoided due to better compressibility of Form CS8, making the preparation process more reliable, improving product appearance and product quality. Better compressibility can increase the compression rate, thus further increases the efficiency of process and reduces the cost of compressibility improving excipients.

According to the objective of the present disclosure, a pharmaceutical composition is provided; said pharmaceutical composition comprises a therapeutically effective amount of Form CS8, Form CS9 or combinations thereof, and pharmaceutically acceptable carriers, diluents or excipients.

Furthermore, the use of Form CS8 and Form CS9 or combinations thereof of the present disclosure for preparing androgen receptor antagonist drugs.

Furthermore, the use of Form CS8 and Form CS9 or combinations thereof of the present disclosure for preparing drugs treating prostate cancer.

In the present disclosure, said "stirring" is accomplished by using a conventional method in the field such as magnetic stirring or mechanical stirring and the stirring speed is 50 to 1800 r/min, preferably the magnetic stirring speed is 300 to 900 r/min and mechanical stirring speed is 100 to 300 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or a higher temperature. The drying temperature is from room temperature to about 60° C., or to 50° C., or to 40° C. The drying time can be 2 to 48 hours, or overnight. Drying is accomplished in a fume hood, forced air convection oven or vacuum oven.

Said "cooling" is accomplished by using conventional methods in the field such as slow cooling and rapid cooling. Slow cooling is usually accomplished at the speed of 0.1° C./min. Rapid cooling is usually accomplished by transferring the sample directly from environment which is no lower than room temperature to refrigerator for cooling.

In the present disclosure, "crystal" or "crystalline form" refers to the solid being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of 0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CS8 and Form CS9 of the present disclosure are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

The term "about", as used herein when referring to a measurable value such as an amount of a compound or formulation of this invention, time, temperature, and the like, is meant to encompass variations of 10%, 5%, 1%, 0.5%, or even 0.1% of the specified value.

DETAILED DESCRIPTION

Figure 1:
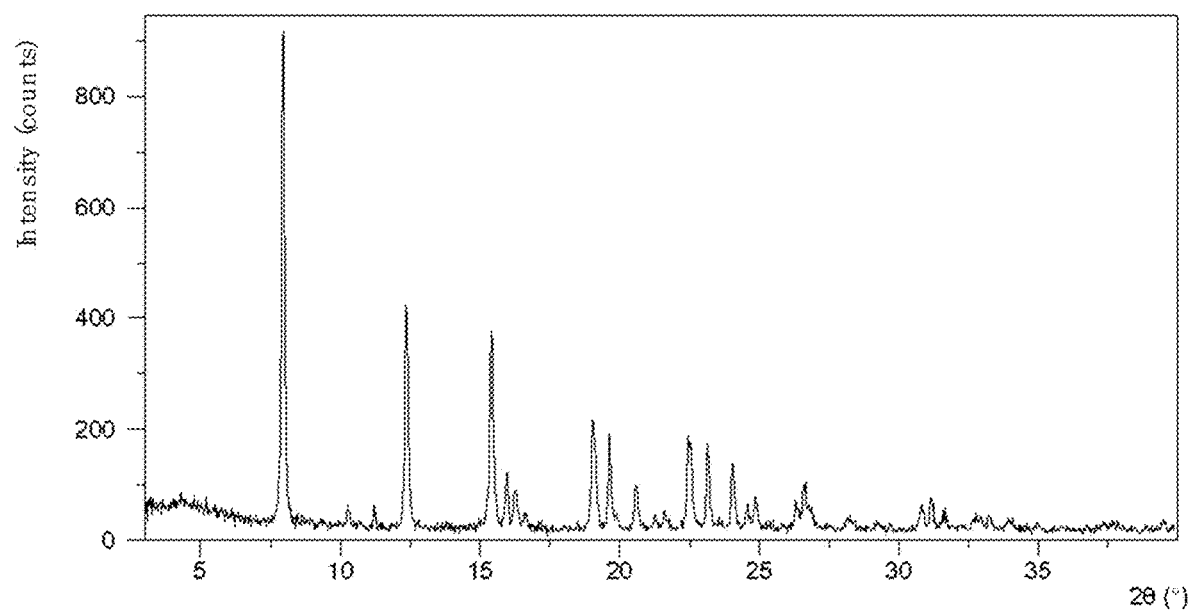
FIG. 1 shows an XRPD pattern of Form CS8 according to example 1.

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

The abbreviations used in the present disclosure are explained as follows:
XRPD: X-ray Powder Diffraction
DSC: Differential Scanning Calorimetry
TGA: Thermal Gravimetric Analysis
PSD: Particle Size Distribution
HPLC: High Performance Liquid Chromatography Instruments and methods used for data collection:

X-ray powder diffraction patterns in the present disclosure were acquired by a Bruker D2 PHASER X-ray powder diffractometer. The parameters of the X-ray powder diffraction method of the present disclosure are as follows:
X-ray Reflection: Cu, Kα
Kα1 (Å): 1.54060; Kα2 (Å): 1.54439
Kα2/Kα1 intensity ratio: 0.50
Voltage: 30 (kV)
Current: 10 (mA)
Scan range: from 3.0 degree to 40.0 degree
The test conditions of Form CS8:
Temperature range: 20° C.-50° C.;
Relative humidity: 10%-45% RH.
There is no special requirement for the test conditions of Form CS9.

Differential scanning calorimetry (DSC) data in the present disclosure were acquired by a TA Q2000. The parameters of the DSC method of the present disclosure are as follows:
Heating rate: 10° C./min
Purge gas: nitrogen Thermal gravimetric analysis (TGA) data in the present disclosure were acquired by a TA Q500. The parameters of the TGA method of the present disclosure are as follows:
Heating rate: 10° C./min
Purge gas: nitrogen The particle size distribution data in the present disclosure were acquired by an S3500 laser particle size analyzer of Microtrac. Microtrac S3500 is equipped with an SDC (Sample Delivery Controller). The test is carried out in wet mode, and the dispersion medium is Isopar G. The laser particle size analyzer parameters are as follows:

| | |
|---|---|
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 30 s |

*Flow rate 60% is 60% of 65 mL/s.

High Performance Liquid Chromatography (HPLC) data in the present disclosure were collected from Agilent 1260&1200 with Diode Array Detector (DAD).

The HPLC method parameters for purity test in the present disclosure are as follows:
1. Column: Waters XBridge C18 150×4.6 mm, 5 μm
2. Mobile Phase: A: 0.1% Trifluoroacetic acid (TFA) in $H_2O$
B: 0.1% TFA in Acetonitrile
Gradient:

| Time (min) | % B |
|---|---|
| 0.0 | 30 |
| 1.0 | 30 |
| 18.0 | 95 |
| 23.0 | 95 |
| 23.1 | 30 |
| 30.0 | 30 |

3. Flow rate: 1.0 mL/min
4. Injection Volume: 5 μL
5. Detection wavelength: 242 nm
6. Column Temperature: 40° C.
7. Diluent: MeOH The HPLC method parameters for solubility test in the present disclosure are as follows:
1. Column: Waters XBridge C18 150×4.6 mm, 5 μm
2. Mobile Phase: A: 0.1% TFA in $H_2O$
B: 0.1% TFA in Acetonitrile
Gradient:

| Time (min) | % B |
|---|---|
| 0.0 | 50 |
| 5.0 | 90 |
| 6.0 | 90 |
| 6.1 | 50 |
| 10.0 | 50 |

3. Flow rate: 1.0 mL/min
4. Injection Volume: 5 μL
5. Detection wavelength: 242 nm
6. Column Temperature: 40° C.
7. Diluent: MeOH Unless otherwise specified, the following examples were conducted at room temperature. Said "room temperature" refers to 10-30° C.

According to the present disclosure, ARN-509 as a raw material are solid (crystalline or amorphous), wax or oil form. Preferably, ARN-509 as a raw material is solid powder.

Raw materials of ARN-509 used in the following examples were prepared by known methods in the prior art, for example, the method disclosed in WO2013184681A.

Example 1~3: Preparation of Form CS8

Example 1

About 2.0 g of ARN-509 was weighed and dissolved in 40.0 mL of methanol. After filtration, the obtained filtrate was cooled to 10° C. at a rate of 0.1° C./min rate, and stirred for about 2 hours. The obtained solid was separated by filtration.

The XRPD, TGA and DSC tests were performed on the obtained solid, and the obtained solid was confirmed to be Form CS8.

The XRPD pattern is substantially as depicted in FIG. 1, and the XRPD data are listed in Table 1.

Figure 2:
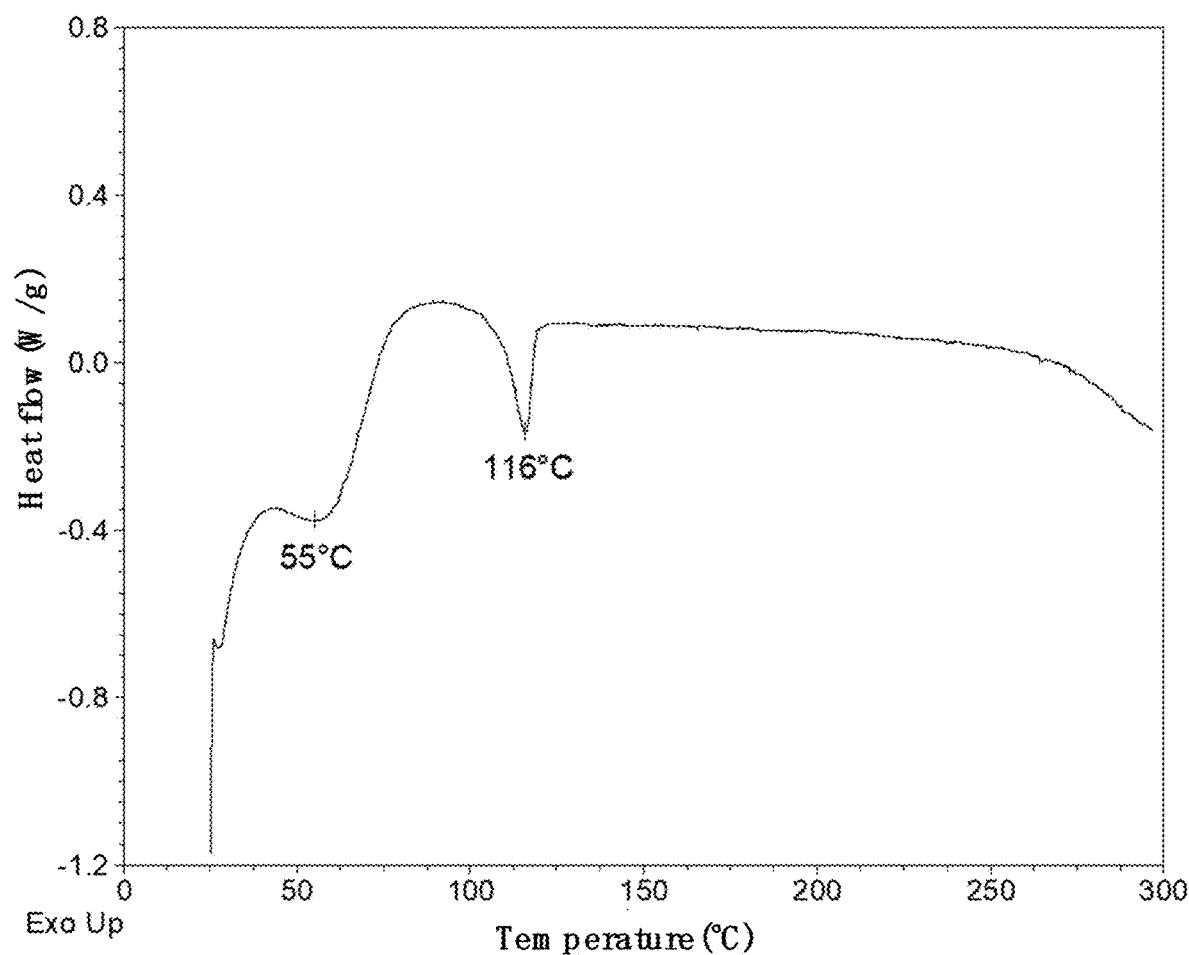
FIG. 2 shows a DSC curve of Form CS8 according to example 1.

The DSC curve of Form CS8 is substantially as depicted in FIG. 2. The first endothermic peak appears around 55° C. and the second endothermic peak appears around 116° C.

Figure 3:
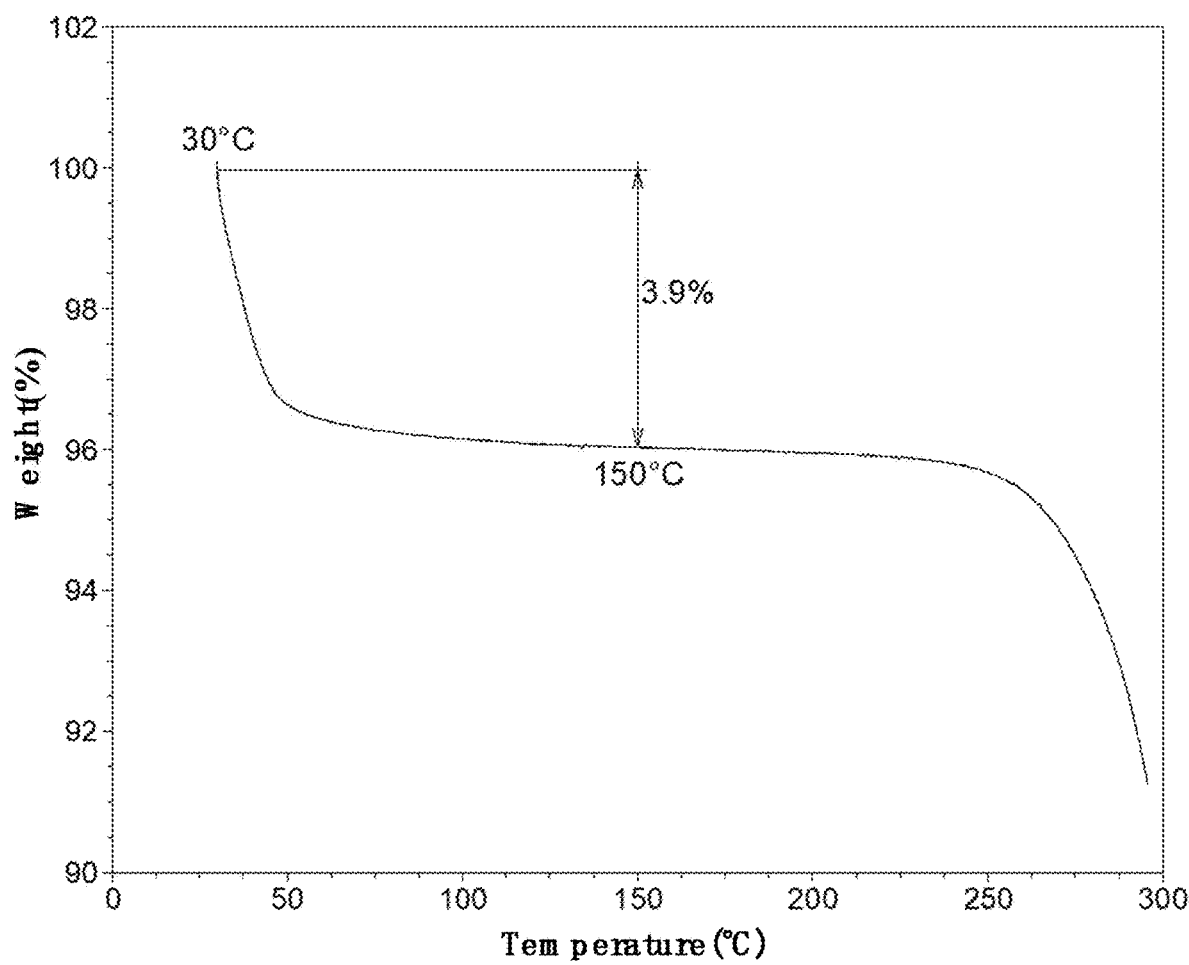
FIG. 3 shows a TGA curve of Form CS8 according to example 1.

The TGA curve of Form CS8 is substantially as depicted in FIG. 3. The TGA curve of Form CS8 shows about 3.9% weight loss when heated to 150° C.

TABLE 1

| Diffraction angle 2θ | d spacing | Intensity % |
| --- | --- | --- |
| 7.94 | 11.13 | 100.00 |
| 10.25 | 8.63 | 2.46 |
| 11.22 | 7.89 | 4.96 |
| 12.37 | 7.16 | 48.18 |
| 15.43 | 5.74 | 41.82 |
| 15.97 | 5.55 | 12.97 |
| 16.30 | 5.44 | 7.55 |
| 19.05 | 4.66 | 21.96 |
| 19.63 | 4.52 | 19.08 |
| 20.59 | 4.31 | 9.43 |
| 22.50 | 3.95 | 18.39 |
| 23.16 | 3.84 | 17.05 |
| 24.05 | 3.70 | 11.39 |
| 24.89 | 3.58 | 6.39 |
| 26.65 | 3.35 | 8.54 |
| 28.28 | 3.16 | 2.88 |
| 30.84 | 2.90 | 5.23 |
| 31.20 | 2.87 | 6.03 |
| 32.82 | 2.73 | 2.11 |

Example 2

About 1.37 g of ARN-509 was weighed and dissolved in 20.0 mL of ethyl formate. After filtration, the obtained filtrate was cooled to −5° C., and stirred overnight. The obtained solid was collected and drying under vacuum at 60° C. for about 48 h to get crystals.

The XRPD test was performed on the obtained solid, and the obtained solid was confirmed to be Form CS8.

Figure 4:
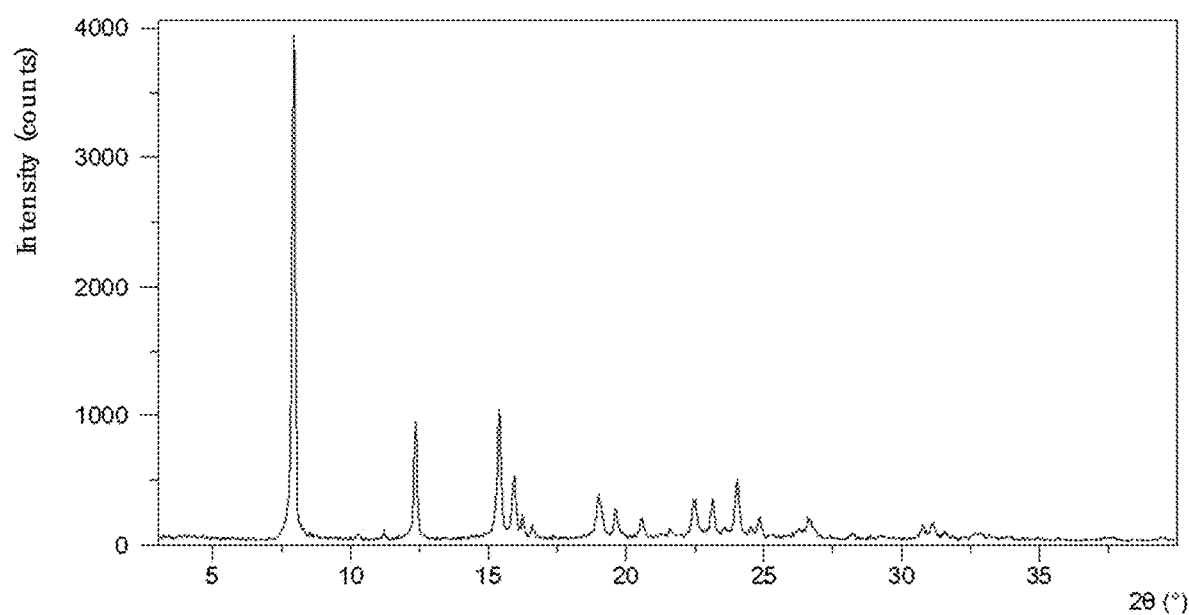
FIG. 4 shows an XRPD pattern of Form CS8 according to example 2.

The XRPD pattern is substantially as depicted in FIG. 4, and the XRPD data are listed in Table 2.

TABLE 2

| Diffraction angle 2θ | d spacing | Intensity % |
| --- | --- | --- |
| 7.95 | 11.13 | 100.00 |
| 12.35 | 7.17 | 22.40 |
| 15.40 | 5.75 | 25.32 |
| 15.94 | 5.56 | 12.81 |
| 16.25 | 5.46 | 4.84 |
| 19.01 | 4.67 | 8.24 |
| 19.61 | 4.53 | 6.24 |
| 20.58 | 4.32 | 4.04 |
| 22.45 | 3.96 | 7.69 |
| 23.14 | 3.84 | 7.48 |
| 24.02 | 3.71 | 11.15 |
| 24.51 | 3.63 | 2.05 |
| 24.85 | 3.58 | 4.62 |
| 26.65 | 3.35 | 3.82 |
| 30.77 | 2.91 | 2.51 |
| 31.13 | 2.87 | 3.38 |

Example 3

About 48.8 mg of ARN-509 was weighed and dissolved in 0.8 mL of methanol/methyl acetate/cyclohexane (1:3:12, v/v/v). The obtained solution was stirred at 5° C. for about 24 h, separated by filtration, and drying the obtained solid with forced air convection at 30° C. to obtain solid.

The XRPD and TGA tests were performed on the obtained solid, and the obtained solid was confirmed to be Form CS8.

Figure 5:
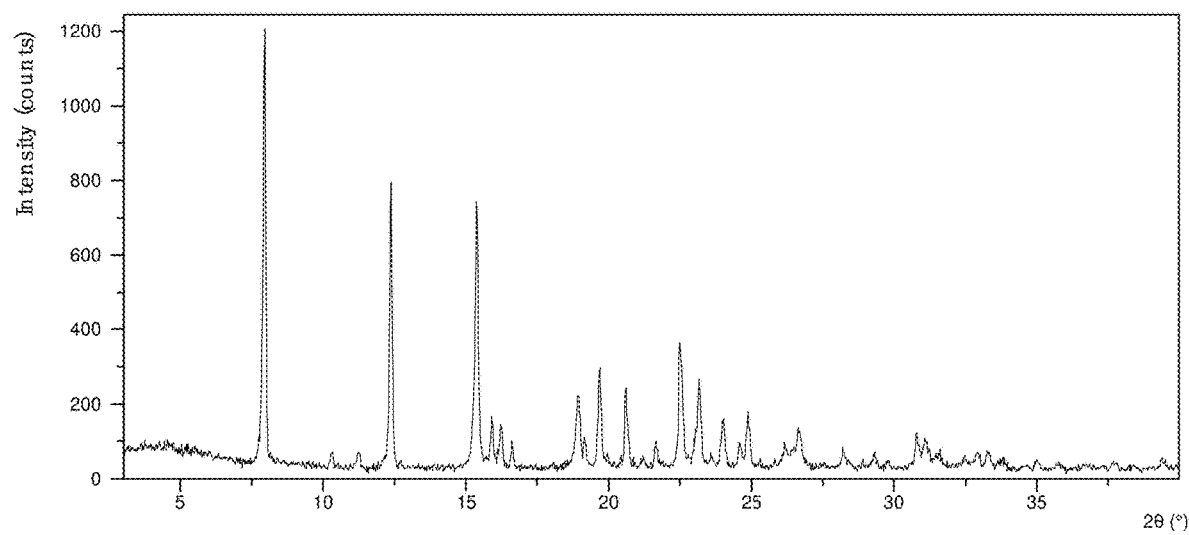
FIG. 5 shows an XRPD pattern of Form CS8 according to example 3.

The XRPD pattern is substantially as depicted in FIG. 5, and the XRPD data are listed in Table 3.

Figure 6:
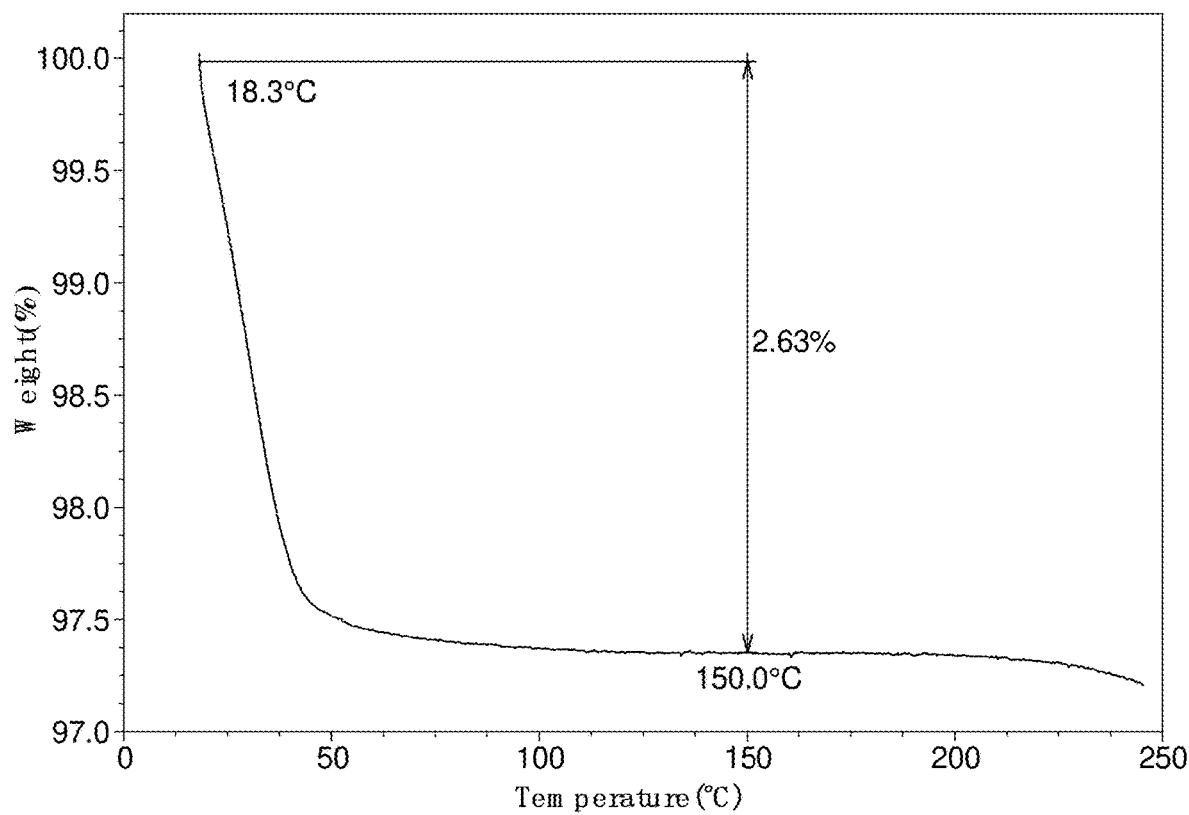
FIG. 6 shows a TGA curve of Form CS8 according to example 3.

The TGA curve of Form CS8 is substantially as depicted in FIG. 6, which shows about 2.6% weight loss when heated to 150° C.

TABLE 3

| Diffraction angle 2θ | d spacing | Intensity % |
| --- | --- | --- |
| 7.94 | 11.13 | 100.00 |
| 10.31 | 8.58 | 2.38 |
| 11.22 | 7.88 | 3.22 |
| 12.37 | 7.16 | 65.85 |
| 15.39 | 5.76 | 61.09 |
| 15.92 | 5.57 | 10.94 |
| 16.24 | 5.46 | 9.76 |
| 16.62 | 5.34 | 6.34 |
| 18.93 | 4.69 | 16.48 |
| 19.16 | 4.63 | 7.00 |
| 19.68 | 4.51 | 23.28 |
| 20.60 | 4.31 | 19.19 |
| 21.65 | 4.11 | 6.13 |
| 22.50 | 3.95 | 27.31 |
| 23.16 | 3.84 | 19.70 |
| 24.00 | 3.71 | 11.42 |
| 24.60 | 3.62 | 5.62 |
| 24.87 | 3.58 | 12.79 |
| 26.68 | 3.34 | 8.60 |
| 28.23 | 3.16 | 4.37 |
| 29.32 | 3.05 | 3.27 |
| 30.78 | 2.90 | 8.15 |
| 31.09 | 2.88 | 6.62 |
| 32.92 | 2.72 | 3.26 |
| 33.28 | 2.69 | 3.56 |

Example 4~10: Preparation of Form CS9

Example 4-8

A certain amount of ARN-509 was weighed, and dissolved in corresponding volume of solvents as shown in Table 4. The obtained solution was stirred at room temperature or 50° C. overnight, filtered and separated to obtain solid. The solid obtained in examples 4-8 were labeled as samples 4-8.

The XRPD, TGA and DSC tests were performed on the obtained solid of sample 4-8, and the obtained solid was confirmed to be Form CS9.

Figure 7:
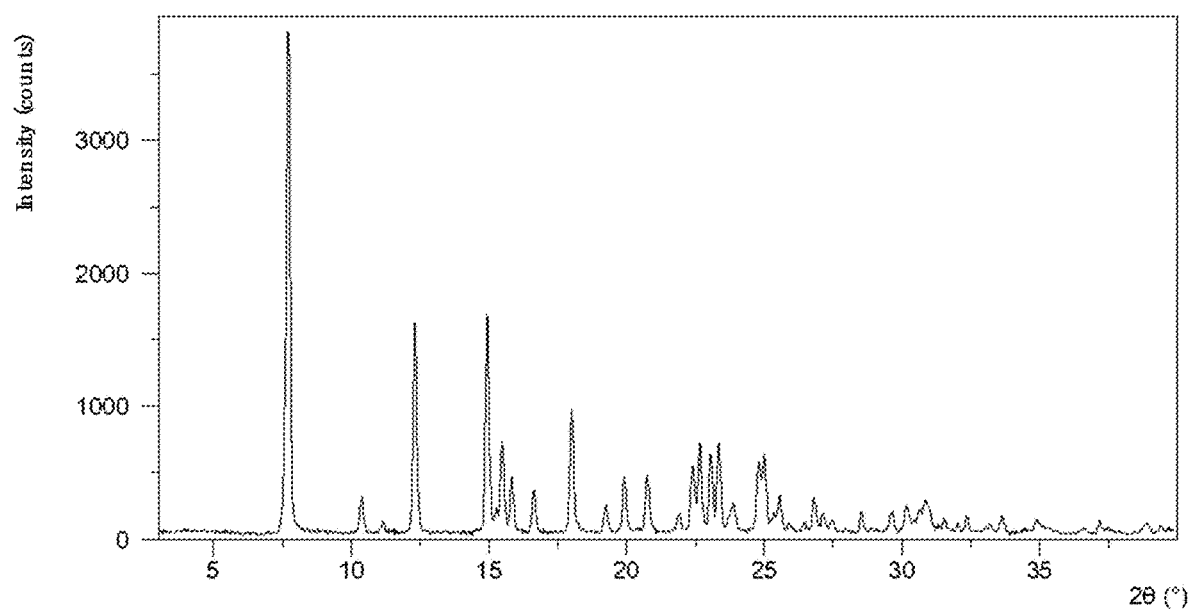
FIG. 7 shows an XRPD pattern of Form CS9 according to example 4.

The XRPD, TGA and DSC test results of sample 4 are as follows:

The XRPD pattern is substantially as depicted in FIG. 7, and the XRPD data are listed in Table 5.

Figure 8:
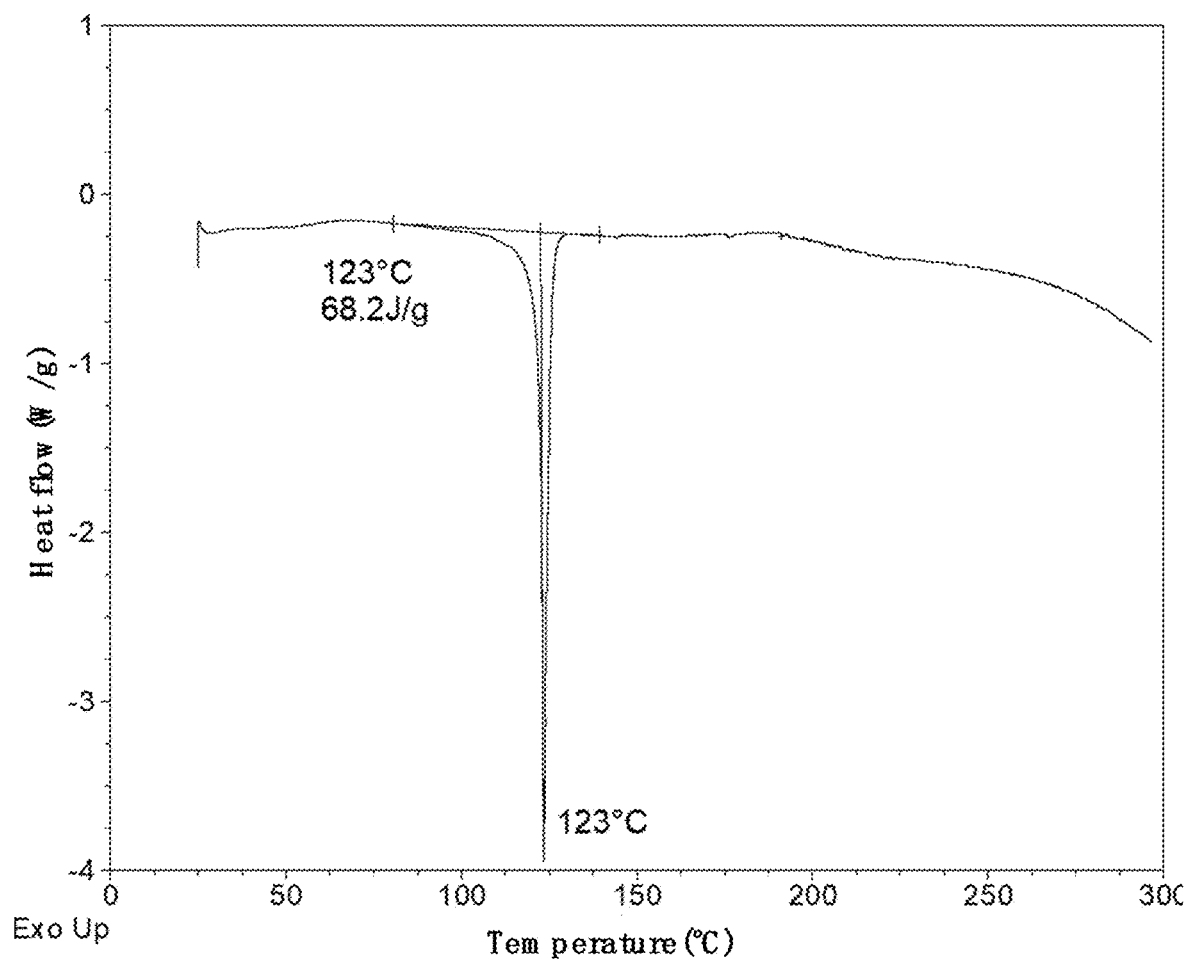
FIG. 8 shows a DSC curve of Form CS9 according to example 4.

The DSC curve is substantially as depicted in FIG. 8. The endothermic peak appears around 123° C.

Figure 9:
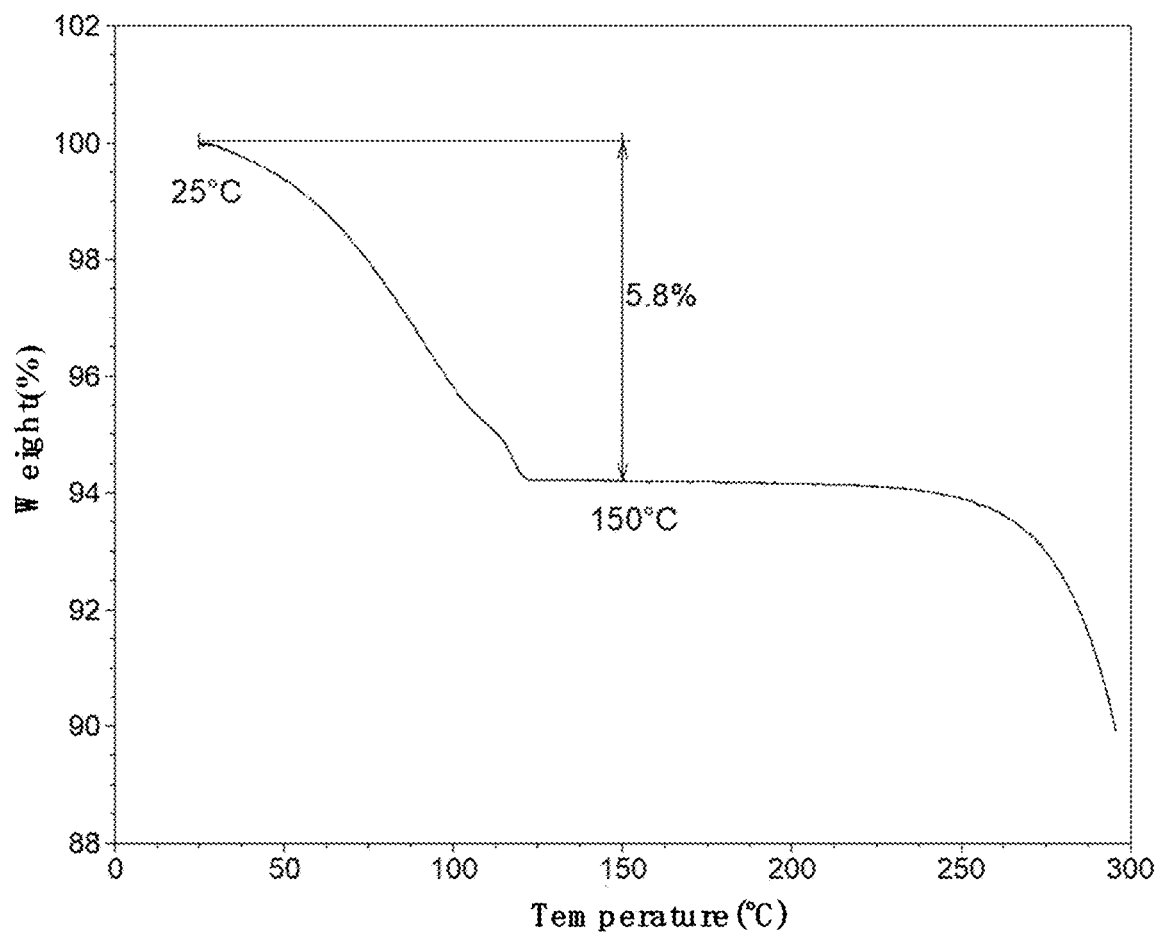
FIG. 9 shows a TGA curve of Form CS9 according to example 4.

The TGA curve is substantially as depicted in FIG. 9, which shows about 5.8% weight loss when heated to 150° C.

TABLE 4

| Example | Mass (mg) | Solvents (volume ratio v/v) | Volume (mL) | Temperature | Samples |
|---|---|---|---|---|---|
| 4 | 5000 | acetonitrile/water (2:1) | 4.0 | room temperature | 4 |
| 5 | 116.6 | Acetonitrile/methanol (1:1) | 0.7 | room temperature | 5 |
| 6 | 107.0 | Acetonitrile/ethanol (1:1) | 0.7 | room temperature | 6 |
| 7 | 108.0 | Acetonitrile/toluene (1:1) | 0.7 | room temperature | 7 |
| 8 | 111.3 | Acetonitrile | 0.7 | 50° C. | 8 |

TABLE 5

| Diffraction angle 2θ | d spacing | Intensity % |
|---|---|---|
| 7.72 | 11.45 | 100.00 |
| 10.38 | 8.52 | 7.72 |
| 11.14 | 7.94 | 2.43 |
| 12.30 | 7.19 | 41.96 |
| 14.95 | 5.93 | 43.59 |
| 15.49 | 5.72 | 17.46 |
| 15.84 | 5.60 | 11.30 |
| 16.64 | 5.33 | 8.61 |
| 18.01 | 4.93 | 24.47 |
| 19.25 | 4.61 | 5.35 |
| 19.92 | 4.46 | 10.92 |
| 20.75 | 4.28 | 11.41 |
| 21.90 | 4.06 | 3.60 |
| 22.40 | 3.97 | 12.81 |
| 22.65 | 3.93 | 17.56 |
| 23.04 | 3.86 | 15.36 |
| 23.35 | 3.81 | 17.63 |
| 23.84 | 3.73 | 5.66 |
| 24.81 | 3.59 | 13.56 |
| 25.01 | 3.56 | 15.15 |
| 25.55 | 3.49 | 7.39 |
| 26.81 | 3.33 | 7.03 |
| 27.15 | 3.28 | 3.99 |
| 27.45 | 3.25 | 2.46 |
| 28.54 | 3.13 | 3.84 |
| 29.62 | 3.02 | 4.14 |
| 30.19 | 2.96 | 5.37 |
| 30.87 | 2.90 | 5.87 |
| 31.53 | 2.84 | 2.65 |
| 32.36 | 2.77 | 3.15 |
| 33.63 | 2.66 | 2.95 |
| 34.89 | 2.57 | 2.59 |
| 37.19 | 2.42 | 3.29 |

Figure 10:
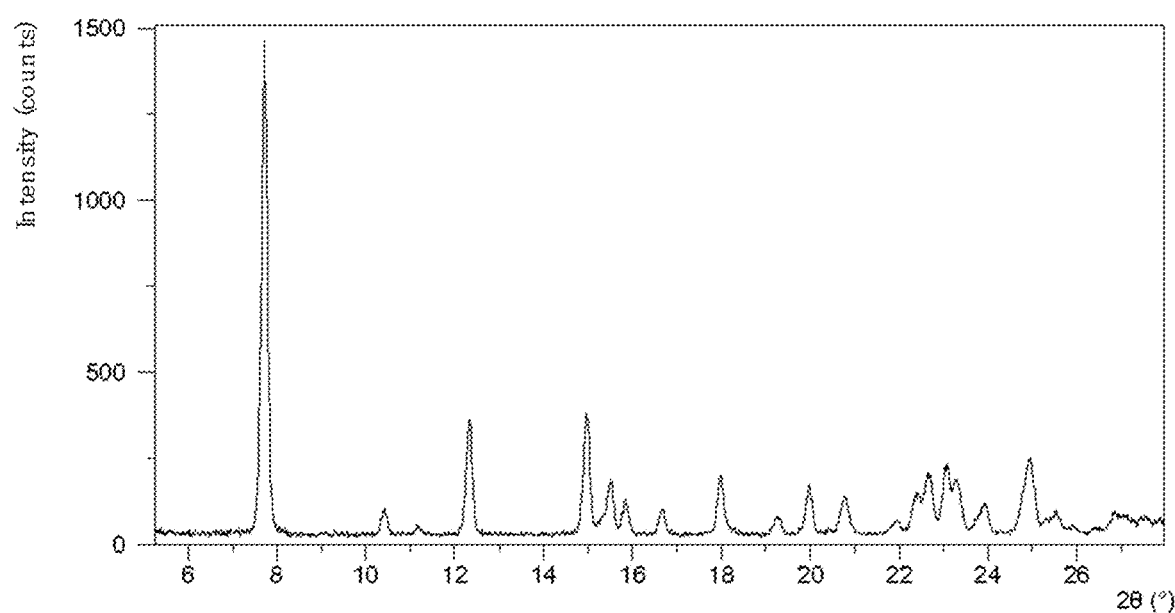
FIG. 10 shows an XRPD pattern of Form CS9 according to example 5.

The XRPD pattern of sample 5 is substantially as depicted in FIG. 10, and the XRPD data are listed in Table 6.

TABLE 6

| Diffraction angle 2θ | d spacing | Intensity % |
|---|---|---|
| 7.72 | 11.46 | 100.00 |
| 10.42 | 8.49 | 6.39 |
| 12.33 | 7.18 | 24.55 |
| 13.96 | 6.34 | 2.20 |
| 14.97 | 5.92 | 27.11 |
| 15.50 | 5.72 | 11.82 |
| 15.83 | 5.60 | 8.42 |
| 16.68 | 5.32 | 5.46 |
| 17.98 | 4.93 | 13.68 |
| 19.25 | 4.61 | 4.21 |
| 19.97 | 4.45 | 10.87 |
| 20.77 | 4.28 | 8.18 |
| 21.92 | 4.06 | 3.45 |
| 22.39 | 3.97 | 8.82 |
| 22.66 | 3.92 | 13.29 |
| 23.05 | 3.86 | 15.94 |
| 23.27 | 3.82 | 12.22 |
| 23.93 | 3.72 | 6.69 |
| 24.94 | 3.57 | 17.29 |
| 25.51 | 3.49 | 5.31 |
| 26.83 | 3.32 | 5.61 |
| 27.52 | 3.24 | 4.55 |

Samples 5-8 and sample 4 have the same or similar XRPD patterns, samples 5-8 and sample 4 are the same crystalline form and have the same properties.

Example 9

About 35.5 mg of ARN-509 was weighed and dissolved in 0.5 mL of methanol/methyl acetate/n-heptane (V/V 1:1:2). The solution was heated to 50° C. (the heating rate is 1° C./min), and then cooled to 15° C. (the cooling rate is 0.1° C./min). Crystal seed Form CS9 was added to the solution, and the solution was cooled from 15° C. to 5° C. (the cooling rate was 0.1° C./min). After holding at 5° C. for 13 hours, transparent crystal was obtained, the obtained solid was Form CS9.

Figure 11:
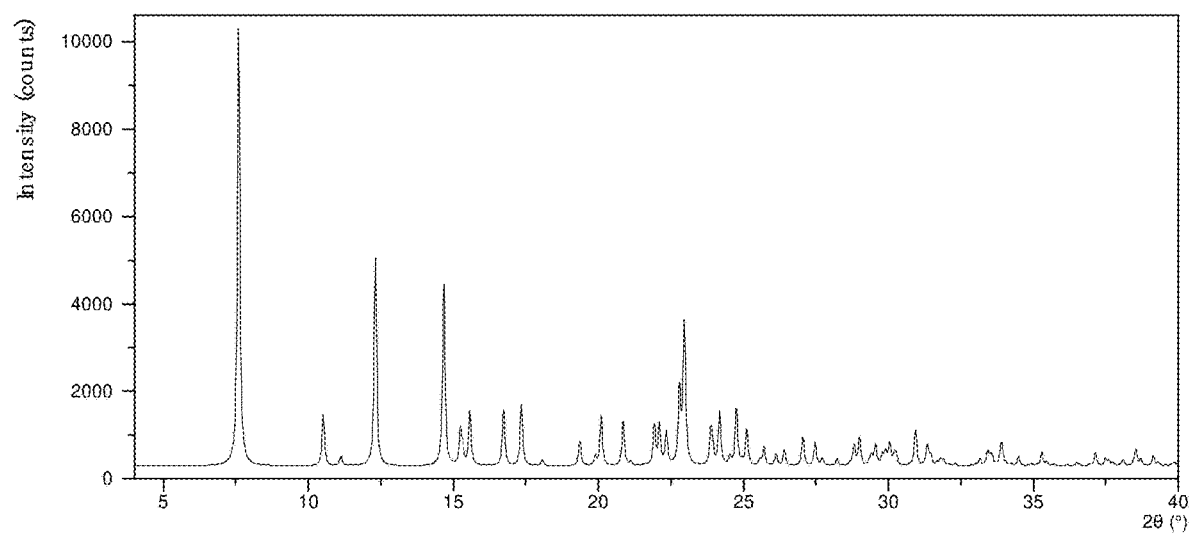
FIG. 11 shows a single crystal XRPD pattern of Form CS9 obtained in Example 9.

Form CS9 is a co-solvate of methyl acetate and water. Its unit cell dimensions are listed in Table 7. The simulated XRPD pattern is substantially as depicted in FIG. 11, and the XRPD data are listed in Table 8.

TABLE 7

| Crystal system | Orthogonal | | | | |
|---|---|---|---|---|---|
| Space group | $Pna2_1$ | | | | |
| Unit cell dimensions | a | 9.1489(11) Å | A | 90.00° |
| | b | 16.077(2) Å | B | 90.00° |
| | c | 16.817(2) Å | Γ | 90.00° |
| Volume of unit cell (V) | 2473.6(5) Å$^3$ | | | | |
| Number of formula units in unit cell (Z) | 4 | | | | |
| Calculated density | 1.395 g/cm$^3$ | | | | |

TABLE 8

| Diffraction angle 2θ | d spacing | Intensity % |
|---|---|---|
| 7.60 | 11.62 | 100.00 |
| 10.51 | 4.62 | 11.56 |
| 12.30 | 8.41 | 49.19 |
| 14.66 | 8.04 | 43.83 |
| 15.24 | 4.26 | 8.63 |
| 15.32 | 3.46 | 3.61 |
| 15.58 | 5.11 | 12.83 |
| 16.74 | 5.29 | 13.29 |
| 17.35 | 6.04 | 15.85 |
| 19.36 | 3.87 | 5.90 |
| 20.10 | 4.90 | 12.36 |
| 20.85 | 4.58 | 11.18 |
| 21.92 | 4.46 | 9.73 |
| 22.10 | 3.90 | 6.10 |

TABLE 8-continued

| Diffraction angle 2θ | d spacing | Intensity % |
|---|---|---|
| 22.34 | 4.40 | 8.80 |
| 22.79 | 7.19 | 19.43 |
| 22.94 | 5.81 | 15.41 |
| 22.97 | 7.95 | 22.21 |
| 23.87 | 4.20 | 8.01 |
| 23.92 | 3.45 | 3.54 |
| 24.17 | 5.78 | 14.12 |
| 24.75 | 5.68 | 13.56 |
| 25.11 | 4.41 | 9.28 |
| 25.72 | 3.73 | 4.83 |
| 26.42 | 3.59 | 4.25 |
| 27.06 | 4.11 | 7.71 |
| 27.48 | 4.02 | 6.29 |
| 28.82 | 3.72 | 4.83 |
| 29.00 | 4.05 | 7.58 |
| 29.56 | 3.98 | 6.17 |
| 29.80 | 3.29 | 2.94 |
| 29.91 | 3.48 | 3.84 |
| 30.05 | 4.02 | 6.34 |
| 30.93 | 4.57 | 10.53 |
| 31.32 | 3.59 | 4.28 |
| 31.46 | 3.37 | 3.18 |
| 33.41 | 3.63 | 4.47 |
| 33.90 | 3.87 | 5.40 |
| 35.29 | 3.41 | 3.30 |
| 37.15 | 3.57 | 4.22 |
| 38.54 | 3.68 | 4.72 |

Example 10

About 80.9 mg of ARN-509 was weighed and dissolved in 0.5 mL of acetonitrile/isopropanol (V/V, 1:1) and cooled to −25° C. to obtain Form CS9.

Figure 12:
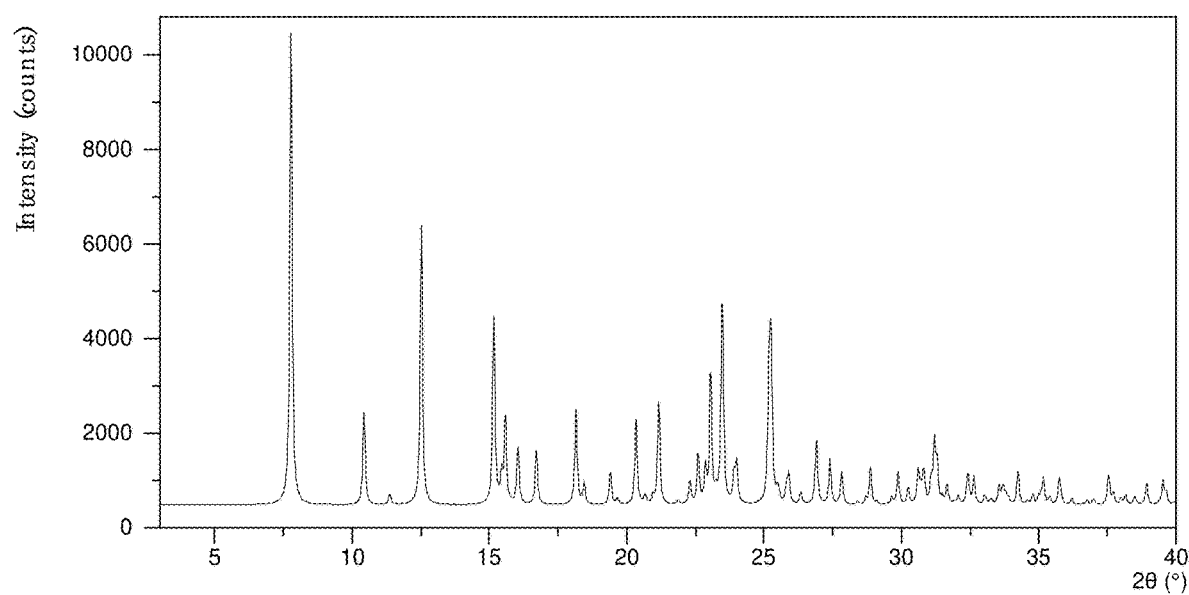
FIG. 12 shows a single crystal XRPD pattern of Form CS9 obtained in Example 10.

Form CS9 obtained in this example is an acetonitrile solvate. Its unit cell dimensions are listed in Table 9. The simulated XRPD pattern is substantially as depicted in FIG. 12, and the XRPD data are listed in Table 10.

TABLE 9

| Crystal system | | Orthogonal | | |
|---|---|---|---|---|
| Space group | | Pna2$_1$ | | |
| Unit cell | a | 9.0288(15) Å | α | 90.00° |
| dimensions | b | 15.295(2) Å | β | 90.00° |
| | c | 16.948(3) Å | γ | 90.00° |
| Volume of unit cell (V) | | 2340.5(6) Å$^3$ | | |
| Number of formula units in unit cell (Z) | | 4 | | |
| Calculated density | | 1.471 g/cm$^3$ | | |

TABLE 10

| Diffraction angle 2θ | d spacing | Intensity % |
|---|---|---|
| 7.78 | 11.35 | 100.00 |
| 10.43 | 8.47 | 20.40 |
| 12.52 | 7.07 | 61.14 |
| 15.17 | 5.84 | 42.32 |
| 15.45 | 5.73 | 5.99 |
| 15.60 | 5.68 | 18.78 |
| 16.05 | 5.52 | 12.78 |
| 16.72 | 5.30 | 12.00 |
| 18.16 | 4.88 | 21.39 |
| 18.45 | 4.81 | 4.96 |
| 19.41 | 4.57 | 7.10 |
| 20.34 | 4.36 | 19.05 |
| 21.16 | 4.20 | 23.91 |
| 22.30 | 3.98 | 4.95 |
| 22.59 | 3.93 | 10.92 |

TABLE 10-continued

| Diffraction angle 2θ | d spacing | Intensity % |
|---|---|---|
| 22.86 | 3.89 | 7.88 |
| 23.05 | 3.86 | 29.49 |
| 23.46 | 3.79 | 28.10 |
| 23.49 | 3.78 | 22.79 |
| 23.90 | 3.72 | 5.88 |
| 23.99 | 3.71 | 8.96 |
| 25.18 | 3.53 | 20.82 |
| 25.23 | 3.53 | 15.65 |
| 25.27 | 3.52 | 26.97 |
| 25.91 | 3.44 | 6.77 |
| 26.92 | 3.31 | 12.61 |
| 27.41 | 3.25 | 11.03 |
| 27.84 | 3.20 | 7.97 |
| 28.88 | 3.09 | 9.03 |
| 29.88 | 2.99 | 7.76 |
| 30.24 | 2.95 | 3.97 |
| 30.62 | 2.92 | 7.91 |
| 30.80 | 2.90 | 5.01 |
| 31.08 | 2.88 | 4.74 |
| 31.20 | 2.86 | 14.22 |
| 31.30 | 2.86 | 9.16 |
| 32.43 | 2.76 | 6.74 |
| 32.64 | 2.74 | 6.58 |
| 33.55 | 2.67 | 4.17 |
| 33.68 | 2.66 | 3.67 |
| 34.24 | 2.62 | 8.39 |
| 35.18 | 2.55 | 6.77 |
| 35.76 | 2.51 | 6.51 |
| 37.55 | 2.39 | 5.03 |

Example 11: Kinetic Solubility of Form CS8, Form A and Form B of the Prior Art

Different parts of the human body have different acidity (pH 1.0-8.0). The pH in stomach is 1.0-2.0, and the pH in the small intestine is 4.0-7.0. The stomach and small intestine are the key organs for drug dissolution and absorption, so measuring the dynamic solubility of a drug in a medium with pH 1.0-7.0 plays an important role in predicting the in vivo bioavailability.

ARN-509 is a poorly water-soluble drug and belongs to BCS II (low solubility and high permeability). Higher solubility is beneficial to improve in vivo dissolution, thus improving in vivo drug efficacy directly.

About 20 mg of Form CS8, Form A and Form B of the prior art were suspended into 2.0 mL of 0.1 mol/L HCl aqueous solution (pH=1.0), 2.0 mL of acetic acid buffer solution (PH=4.5) and 2.0 mL of phosphate buffer solution (pH=6.8) to make suspensions. After equilibrated for 15 minutes, 30 minutes, and 1 hour, concentrations (μg/mL) of the saturated solutions were measured by HPLC. The results are listed in Table 11.

TABLE 11

| Medium | Form A of the prior art | | | Form B of the prior art | | | Form CS8 | | |
|---|---|---|---|---|---|---|---|---|---|
| | 15 min μg/mL | 30 μg/m | 1 h μg/m | 15 μg/m | 30 min μg/mL | 1 h μg/m | 15 μg/m | 30 μg/m | 1 h μg/m |
| HCl aqueous | 7.4 | 6.2 | 8.0 | 1.2 | 1.5 | 1.3 | 23.6 | 25.1 | 18.7 |
| Acetic acid buffer solution | 5.9 | 5.2 | 5.5 | 1.1 | 1.4 | 1.3 | 17.7 | 10.6 | 10.9 |
| phosphate | 6.1 | 8.4 | 4.8 | 1.2 | 1.0 | 0.9 | 22.8 | 18.9 | 20.6 |

The results show that Form CS8 have higher solubility in pH=1.0 hydrochloric acid aqueous solution, PH=4.5 acetic acid buffer solution and pH=6.8 phosphate buffer solution.

Example 12: Stability Assessment of Form CS8

1. The Storage Stability of Form CS8 Under Long-Term and Accelerated Conditions

Figure 13:
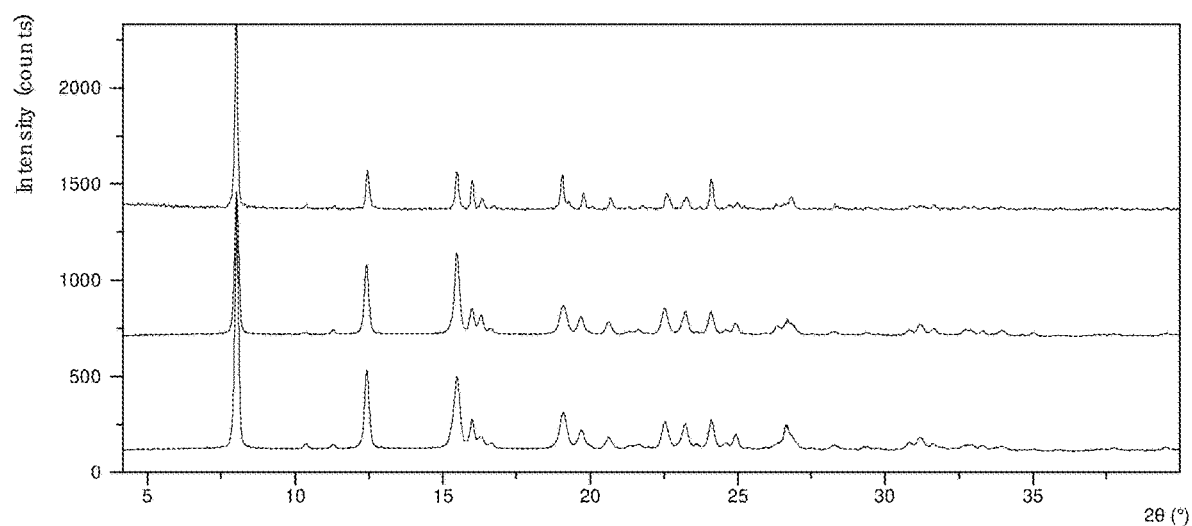
FIG. 13 shows an XRPD pattern overlay of Form CS8 of the present disclosure before and after being stored under 25° C./60% RH (from top to bottom: initial, being stored for 6 months in open dish, being stored for 6 months in closed dish).
Figure 14:
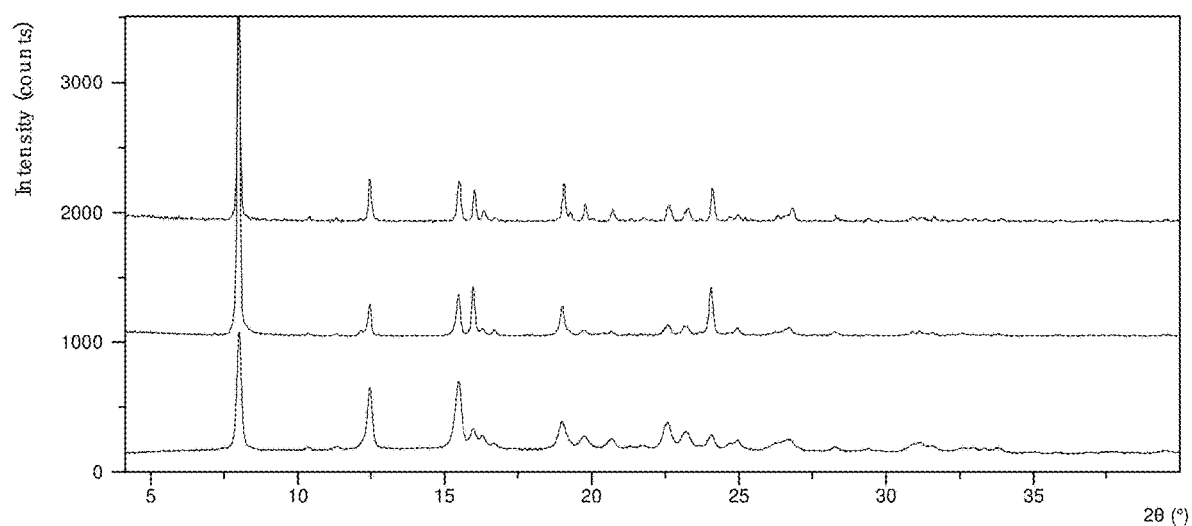
FIG. 14 shows an XRPD pattern overlay of Form CS8 of the present disclosure before and after being stored under 40° C./75% RH (from top to bottom: initial, being stored for 6 months in open dish, being stored for 6 months in closed dish).

Approximately 30 mg of Form CS8 was stored under 25° C./60% RH and 40° C./75% RH in open or close dishes. Crystalline form and chemical impurity were checked by XRPD and HPLC, respectively. The results are shown in Table 12. XRPD pattern overlay of Form CS8 of the present disclosure before and after being stored under 25° C./60% RH are depicted in FIG. 13. XRPD pattern overlay of Form CS8 of the present disclosure before and after being stored under 40° C./75% RH are depicted in FIG. 14.

TABLE 12

| Condition | Time | Initial solid form | Solid form after storage | Initial purity | Purity after storage |
|---|---|---|---|---|---|
| 25° C./60% RH (closed) | 6 months | From CS8 | From CS8 | 99.96% | 99.96% |
| 25° C./60% RH (open) | 6 months | From CS8 | From CS8 | 99.96% | 99.96% |
| 40° C./75% RH (closed) | 6 months | From CS8 | From CS8 | 99.96% | 99.95% |
| 40° C./75% RH (open) | 6 months | From CS8 | From CS8 | 99.96% | 99.95% |

The results show that Form CS8 kept stable for at least 6 months at 25° C./60% RH and 40° C./75% RH. It can be seen that Form CS8 has good stability under both long-term and accelerated conditions.

2. The Storage Stability of Form CS8 Under Stress Condition

Approximately 30 mg of Form CS8 was stored under 60° C./75% RH in open or close dishes. Crystalline form change of Form CS8 was tested by XRPD. The results are shown in Table 13.

TABLE 13

Figure 15:
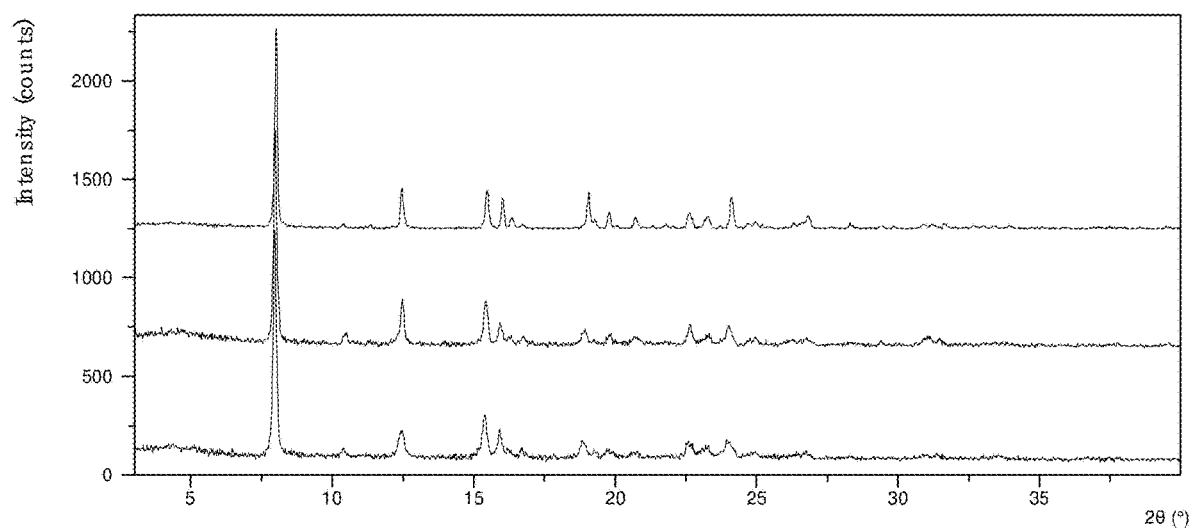
FIG. 15 shows an XRPD pattern overlay of Form CS8 of the present disclosure before and after being stored under 60° C./75% RH (from top to bottom: initial, being stored for 2 weeks in open dish, being stored for 2 weeks in closed dish).

| Condition(container open or close) | Time | Initial solid form | Solid form after storage | FIGS |
|---|---|---|---|---|
| 60° C./75% RH | 2 weeks | Form CS8 | Form CS8 | FIG. 15 |

The results show that Form CS8 kept stable for at least 2 weeks at 60° C./75% RH. It can be seen that Form CS8 has good stability under stress condition with high temperature and humidity.

Example 13: Mechanical Stability of Form CS8

Figure 16:
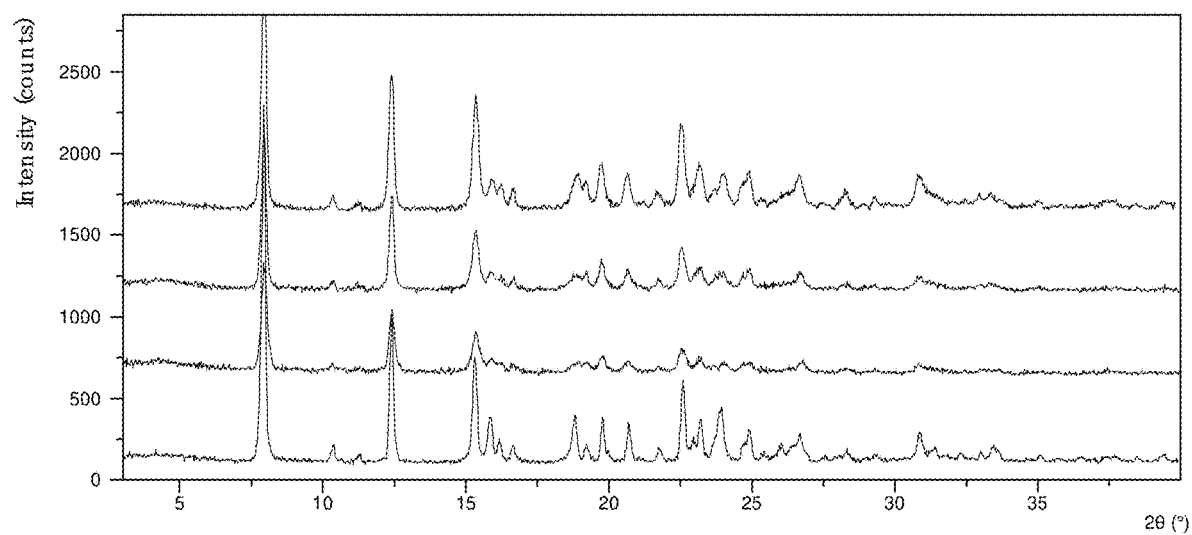
FIG. 16 shows an XRPD pattern overlay of Form CS8 of the present disclosure after being tableted under different pressures (from top to bottom: 3 KN, 7 KN, 14 KN, before being tableted).

A certain amount of Form CS8 was compressed into pellets under different pressures with suitable tableting die. Crystalline form before and after tableting were checked by XRPD. The test results are shown in Table 14, XRPD pattern overlay is depicted in FIG. 16.

TABLE 14

| Crystalline form before tableting | Pressure | Crystalline form after tableting |
|---|---|---|
| Form CS8 | 3 kN | Form CS8 |
| | 7 kN | Form CS8 |
| | 14 kN | Form CS8 |

The results show that Form CS8 has good stability under different pressures.

Figure 17:
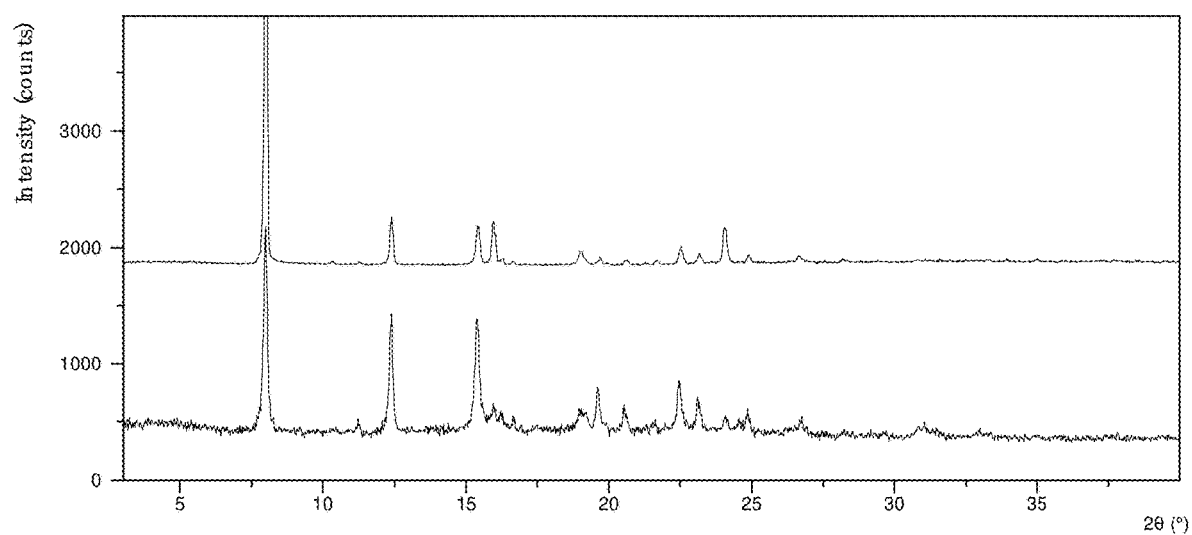
FIG. 17 shows an XRPD pattern overlay of Form CS8 of the present disclosure before and after being ground (top: before grinding; bottom: after grinding).
Figure 18:
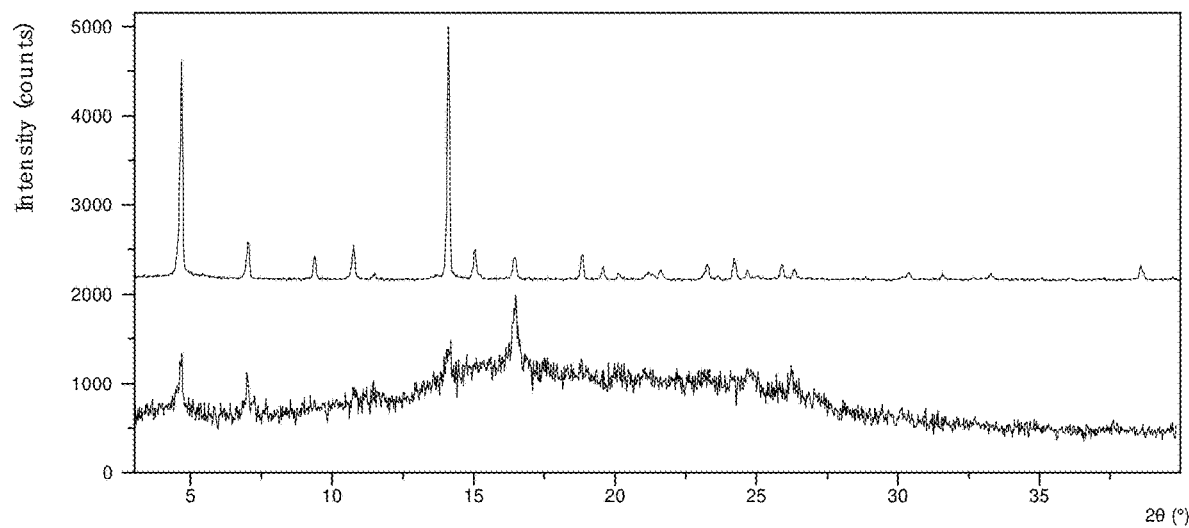
FIG. 18 shows an XRPD pattern overlay of Form A of the prior art before and after being ground (top: before grinding; bottom: after grinding).
Figure 19:
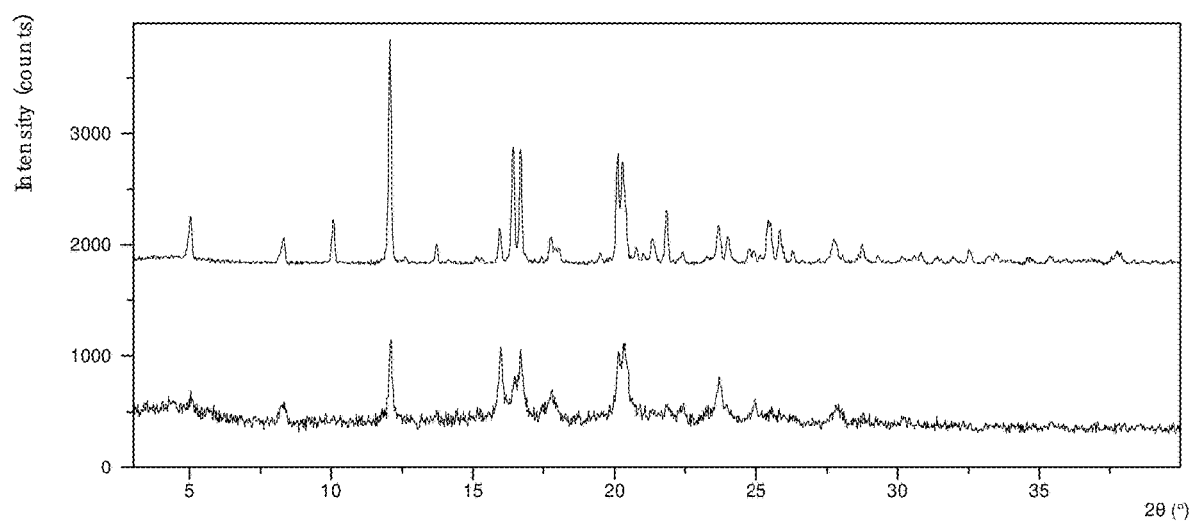
FIG. 19 shows an XRPD pattern overlay of Form B of the prior art before and after being ground (top: before grinding; bottom: after grinding).

Form CS8, Form A and Form B of the prior art were ground manually for 5 minutes in a mortar, XRPD patterns were collected before and after gridding. The XRPD pattern overlay of Form CS8, Form A and Form B of the prior art are depicted in FIG. 17, FIG. 18 and FIG. 19. The results are listed in Table 15.

TABLE 15

| Before grinding | After grinding |
|---|---|
| Form CS8 | Crystalline form and crystallinity are basically unchanged |
| Form A of the prior art | Almost change to amorphous |
| Form B of the prior art | Crystallinity decreased |

The results show that compared with Form A and Form B of the prior art, Form CS8 shows better stability under grinding condition.

Figure 20:
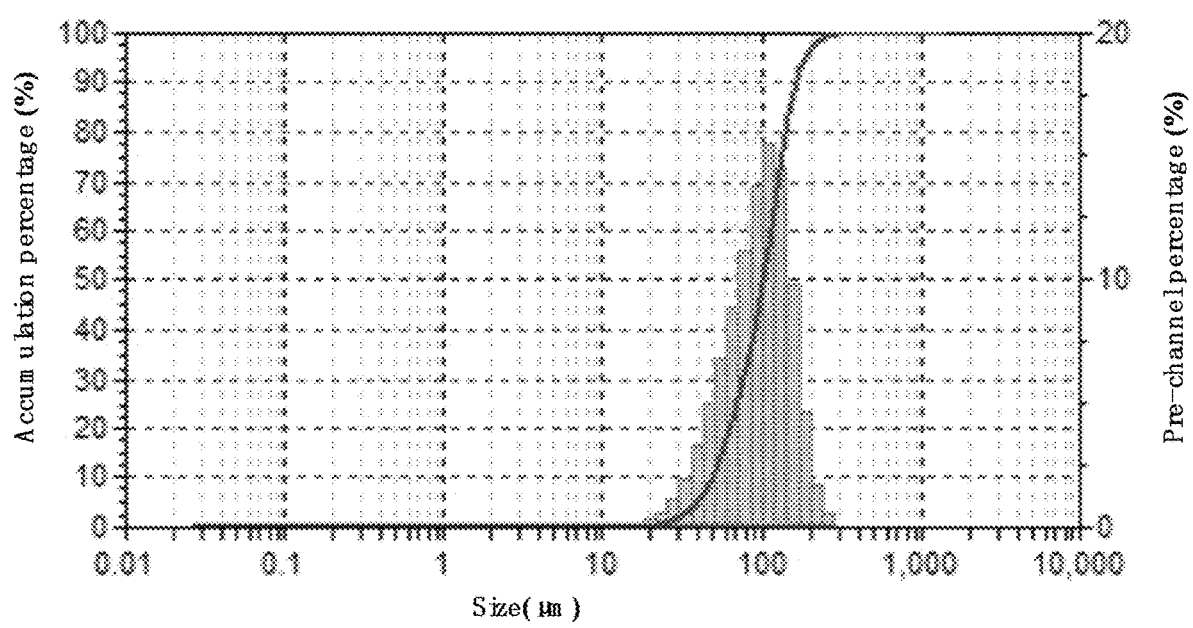
FIG. 20 shows the particle size distribution of Form CS8 of the present disclosure.
Figure 21:
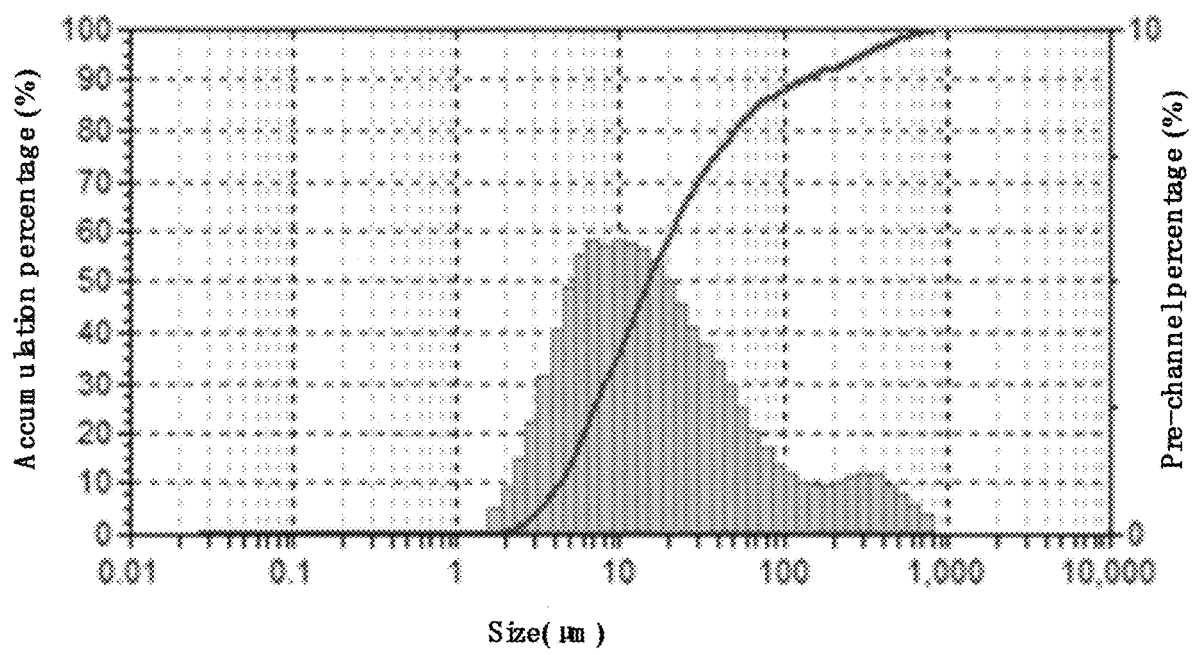
FIG. 21 shows the particle size distribution of Form A of the prior art.
Figure 22:
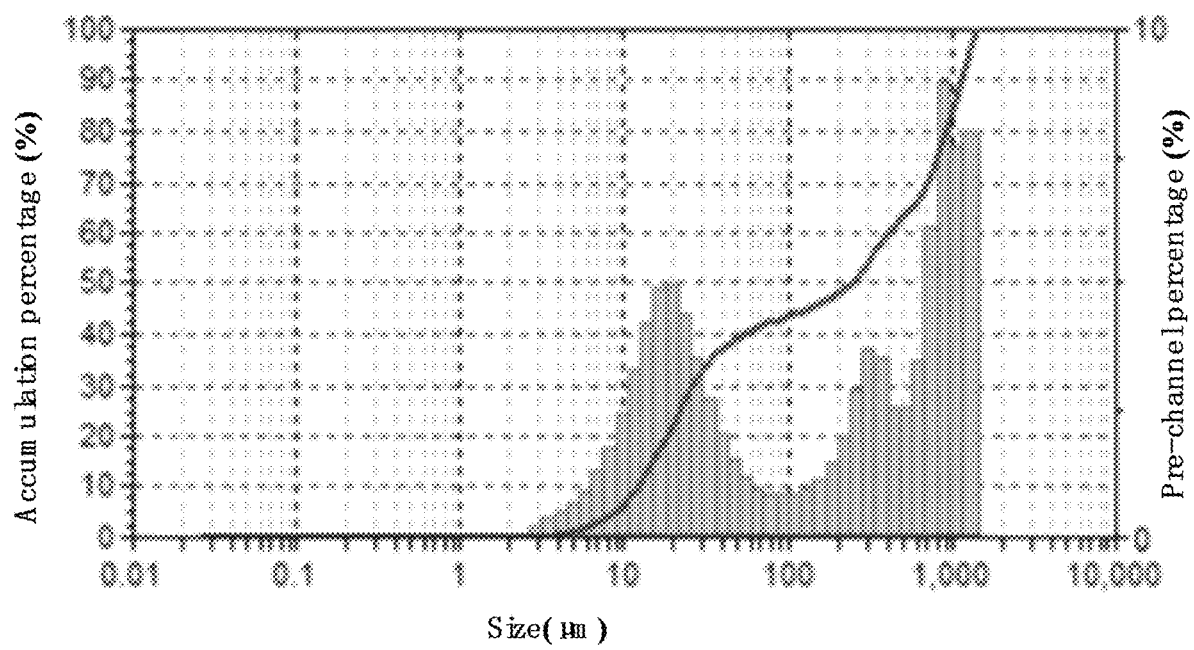
FIG. 22 shows the particle size distribution of Form B of the prior art.

Example 14: Particle Size Distribution of Form CS8, Form A and Form B of the Prior Art Approximately 20 mg of Form CS8, Form A and Form B of the prior art were added into 10 mL of Isopar G (containing 0.2% lecithin). The mixture was mixed thoroughly and transferred into the SDC. The measurement was started when the sample amount indicator is in appropriate position. The average particle diameter calculated by volume, the diameter at which 10% mass is comprised of smaller particles (D10), the diameter at which 50% mass is comprised of smaller particles (D50) and the diameter at which 90% mass is comprised of smaller particles (D90) were obtained in particle size distribution test. The results are shown in Table 16. The particle size distribution diagram of Form CS8, Form A and Form B of the prior art were shown in FIG. 20, FIG. 21, FIG. 22.

TABLE 16

| Form | MV (μm) | D10 (μm) | D50 (μm) | D90 (μm) |
| --- | --- | --- | --- | --- |
| Form CS8 | 104.7 | 48.60 | 100.8 | 164.9 |
| Form A of the prior art | 53.51 | 4.22 | 14.81 | 130.4 |
| Form B of the prior art | 420.3 | 12.1 | 241.7 | 1133 |

The results show that Form CS8 has uniform particle size distribution, which is superior to that of Form A and Form B of the prior art.

Example 15: Adhesiveness of Form CS8, Form A and Form B of the Prior Art

Approximately 30 mg of Form CS8, Form A and Form B of the prior art were weighed and then added into the dies of φ8 mm round tooling, compressed at 10 KN and held for 30 s. The punch was weighed and amount of material sticking to the punch was calculated. The compression was repeated twice and the cumulative amount, maximum amount and average amount of material sticking to the punch during compression process were recorded. Detailed experimental results are shown in Table 17.

TABLE 17

| Form | Average amount (mg) | Maximum amount (mg) |
| --- | --- | --- |
| Form A of the prior art | 0.13 | 0.19 |
| Form B of the prior art | 0.15 | 0.17 |
| Form CS8 | 0.08 | 0.11 |

Test results indicate that the adhesiveness of Form CS8 is superior to Form A and Form B of the prior art.

Example 16: Compressibility of Form CS8, Form A and Form B of the Prior Art 80 mg of Form CS8, Form A and Form B of the prior art were weighed and added into the dies of φ6 mm round tooling, compressed at 10 KN manually, then stored at room temperature for 24 h until complete elastic recovery. Hardness (H) was tested with an Intelligent Tablet Hardness Tester. Diameter (D) and thickness (L) were tested with a caliper. Tensile strength of the powder was calculated with the following formula: T=2H/πDL. Under a certain force, the greater the tensile strength, the better the compressibility. The results are presented in Table 18.

TABLE 18

| Form | Thickness (mm) | Diameter (mm) | Hardness (N) | Tensile strength (MPa) |
| --- | --- | --- | --- | --- |
| Form A of the prior art | 2.10 | 6.08 | 12.3 | 0.64 |
| Form B of the prior art | 2.13 | 6.09 | 10.1 | 0.50 |
| Form CS8 | 2.19 | 6.05 | 14.6 | 0.70 |

The results indicate that CS8 has better compressibility compared with Form A and Form B of the prior art.

Example 17 Preparation of Form CS8, Form A and Form B of the Prior Art Drug Products Form CS8, Form A and Form B of the prior art were blended according to formulation in Table 19 and formulation process in Table 20, then corresponding tablets were prepared.

TABLE 19

| | Number | Component | mg/unit | % (w/w) |
| --- | --- | --- | --- | --- |
| Intra-granular components | 1 | API (ARN-509) (Form CS8, Form A or Form B of the prior art) | 25.00 | 25.00 |
| | 2 | Microcrystalline Cellulose (PH 101) | 71.50 | 71.50 |
| | 3 | Crospovidone (XL) | 2.00 | 2.00 |
| | 4 | Magnesium stearate (5712) | 0.25 | 0.25 |
| Extra-granular components | 5 | Crospovidone (XL) | 1.00 | 1.00 |
| | 6 | Magnesium stearate (5712) | 0.25 | 0.25 |
| | | Total | 100.00 | 100.00 |

TABLE 20

| Stage | Process |
| --- | --- |
| Preliminary mixing | Weighed intra-granular excipients in Table 19 and blend for 2 min in a PE bag |
| Sift out | Pass the mixture through a 35 mesh sieve and then put in a PE bag and mixed for 1 min; |
| Dry granulation | Tableted by a single punch manual tablet press (type: ENERPAC; die: φ 20 mm round; tablet weight: 500 mg; pressure: 5 ± 0.5 KN); |
| Pulverize | The obtained tablet was pulverized and sieved through a 20 mesh sieve; |
| Mixed again | Weighed extra-granular excipients and pulverized particles and blend for 2 min in a PE bag; |
| Tablet | Tableted by a single punch manual tablet press (type: ENERPAC; die: φ 20 mm round; tablet weight: 500 mg; pressure: 5 ± 0.5 KN); |
| Package | Put into a 35 cc HDPE bottles, 3 capsules per bottle with 1 g of desiccant |

Example 18 In Vitro Dissolution Profile of Form CS8, Form A and Form B of the Prior Art Drug Products In vitro dissolution test was performed on Form CS8, Form A and Form B of the prior art drug products obtained from example 17. Dissolution method according to Chinese Pharmacopoeia 2015<0931> was used. The conditions are as follows:

Medium: pH=4.5 acetate buffer solution+0.5% (w/w) sodium lauryl sulfate aqueous solution Method: Paddle Volume: 900 mL Speed: 75 rpm Temperature: 37° C.

Figure 23:
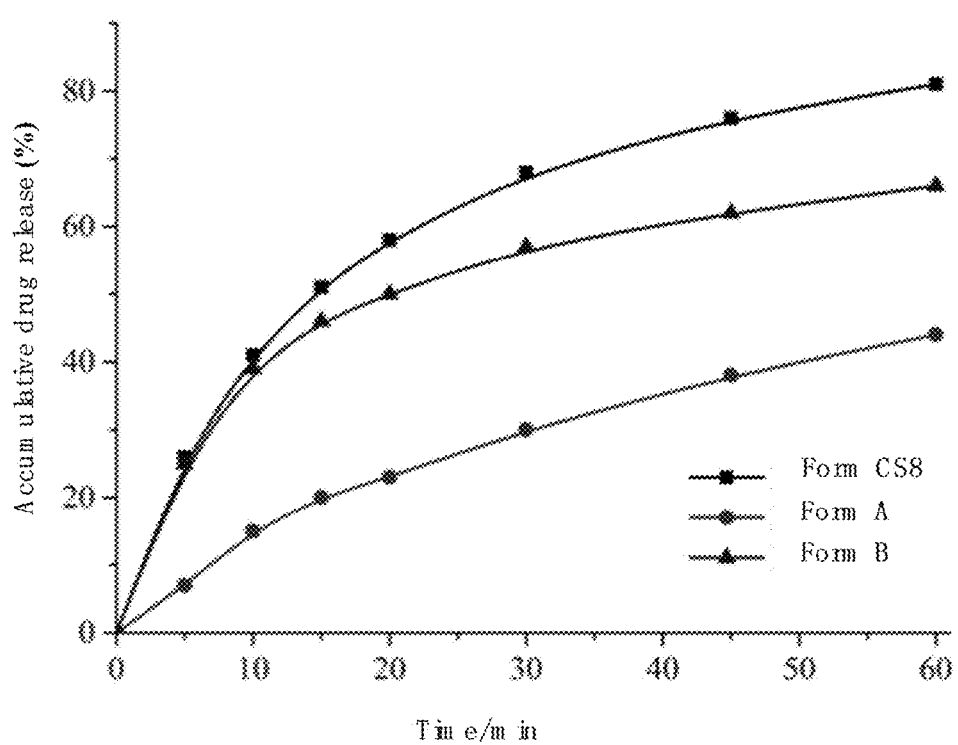
FIG. 23 shows the dissolution profiles of Form CS8, Form A of the prior art and Form B of the prior art.

In vitro dissolution results of Form CS8, Form A and Form B of the prior art drug products are presented in Table 21 and FIG. 23, which indicate that compared with Form A and Form B of the prior art, Form CS8 drug product possesses better dissolution.

TABLE 21

| | Cumulative drug release (%) | | |
| --- | --- | --- | --- |
| Time(min) | Form CS8 | Form A of the prior art | Form B of the prior art |
| 0 | 0 | 0 | 0 |
| 5 | 26 | 7 | 25 |
| 10 | 41 | 15 | 39 |
| 15 | 51 | 20 | 46 |
| 20 | 58 | 23 | 50 |

TABLE 21-continued

| | Cumulative drug release (%) | | |
|---|---|---|---|
| Time(min) | Form CS8 | Form A of the prior art | Form B of the prior art |
| 30 | 68 | 30 | 57 |
| 45 | 76 | 38 | 62 |
| 60 | 81 | 44 | 66 |

Example 19 Stability of Form CS8 in Drug Product

Figure 24:
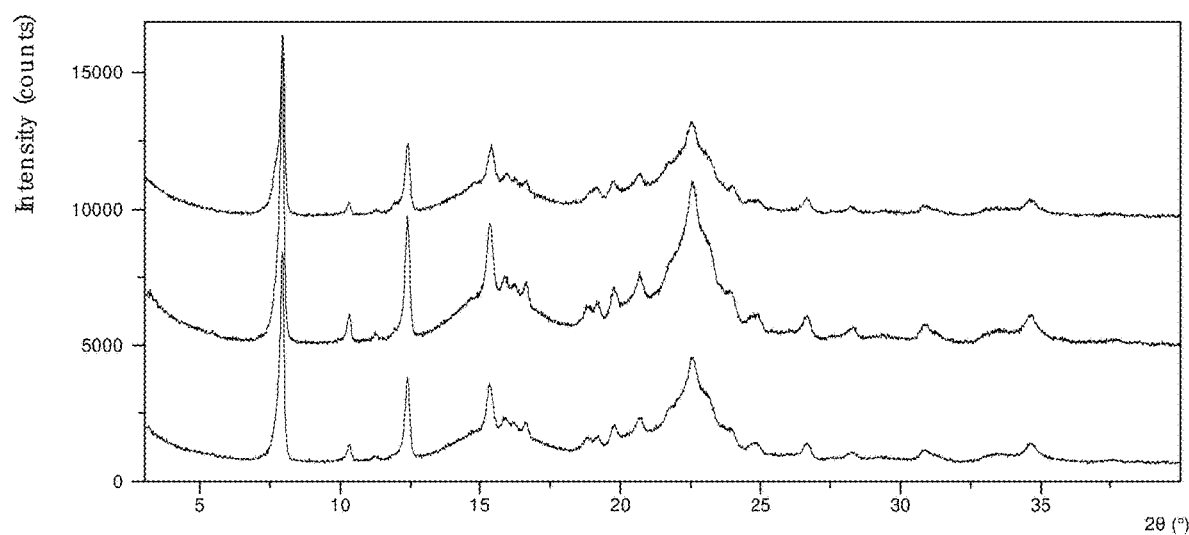
FIG. 24 shows an XRPD pattern overlay of Form CS8 drug product of the present disclosure before and after being stored under 25° C./60% RH (from top to bottom: 3 months, 1 month, initial).
Figure 25:
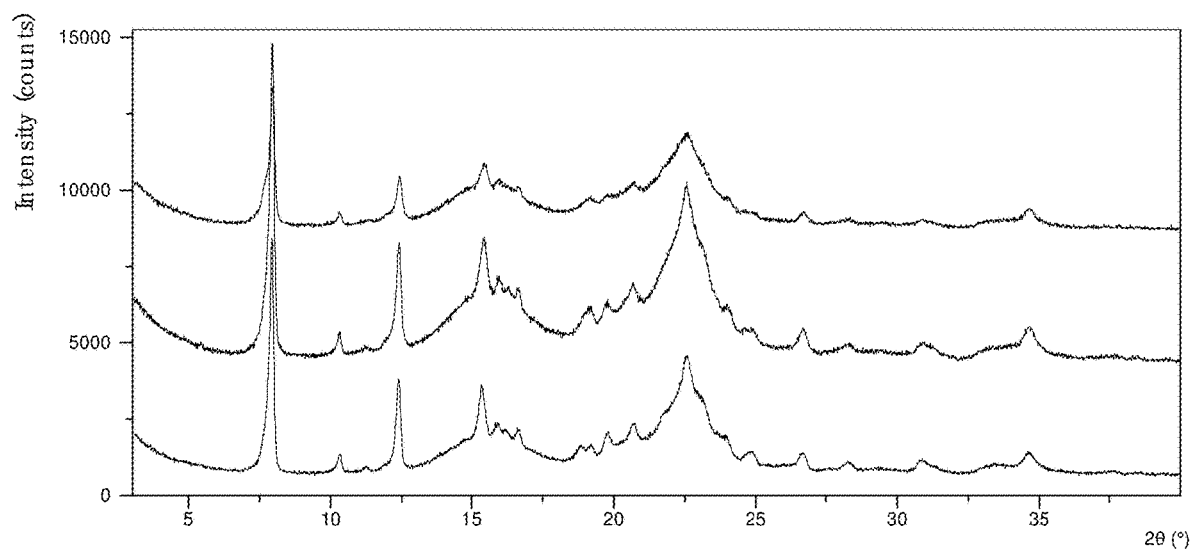
FIG. 25 shows an XRPD pattern overlay of Form CS8 drug product of the present disclosure before and after being stored under 40° C./75% RH (from top to bottom: 3 months, 1 month, initial).

The tablets of Form CS8 were packed in HDPE bottles and stored under 25° C./60% RH and 40° C./75% RH conditions. Crystalline form and impurity of the sample were tested to check the stability of Form CS8 drug product after being stored for 3 months. The results indicate that Form CS8 drug product can keep physically and chemically stable under 25° C./60% RH and 40° C./75% RH for at least 3 months. The crystalline form does not change, and the purity remains substantially unchanged. The results are shown in Table 22. The XRPD patterns overlay before and after being stored at 25° C./60% RH and 40° C./75% RH are shown in FIG. 24 and FIG. 25, respectively.

TABLE 22

| Condition | Time | Initial form | Solid form after storage | Initial purity | Purity after storage |
|---|---|---|---|---|---|
| 25° C./60% RH | 3 months | Form CS8 | Form CS8 | 99.76% | 99.76% |
| 40° C./75% RH | 3 months | Form CS8 | Form CS8 | 99.76% | 99.76% |

The results indicate that Form CS8 has good physically and chemically stable in drug products.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline form CS8 of ARN-509,

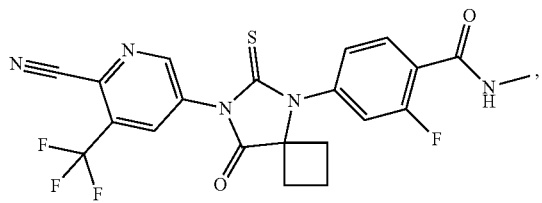 [SMILES: CNC(=O)c1ccc(N2C(=S)N(c3cnc(C#N)c(C(F)(F)F)c3)C(=O)C23CCC3)cc1F]

wherein the X-ray powder diffraction pattern shows characteristic peaks at 2theta values of 7.9±0.2°, 12.4±0.2°, and 19.0±0.2° using CuKα radiation.

2. The crystalline form CS8 according to claim 1, wherein the X-ray powder diffraction pattern shows one or two or three characteristic peaks at 2theta values of 15.4±0.2°, 19.6±0.2° and 22.5±0.2° using CuKα radiation.

3. The crystalline form CS8 according to claim 1, wherein the X-ray powder diffraction pattern shows one or two or three characteristic peaks at 2theta values of 23.2±0.2°, 16.0±0.2° and 24.0±0.2° using CuKα radiation.

4. A process for preparing crystalline form CS8 of ARN-509 according to claim 1, wherein the process comprises:
(1) dissolving ARN-509 into a solvent of an alcohol, cooling to −20° C. to 16° C., precipitating a solid to obtain crystalline form CS8; or
(2) dissolving ARN-509 into ethyl formate, cooling to −20° C. to 10° C. to obtain a solid, and drying the obtained solid under vacuum at 5° C. to 70° C. to obtain crystalline form CS8; or
(3) dissolving ARN-509 into a solvent mixture of methyl acetate, an alcohol and an alkane, stirring at 0° C. to 10° C., separating by filtration to obtain a solid, and drying the obtained solid with forced air convection at 20° C. to 40° C. to obtain crystalline form CS8.

5. The process for preparing crystalline form CS8 of ARN-509 according to claim 4, wherein in method (1), said alcohol is methanol, said cooling temperature is 10° C.; in method (2), said cooling temperature is −5° C., said vacuum-drying temperature is 60° C.; in method (3), said alcohol is methanol, said alkane is cyclohexane, said stirring temperature is 5° C., said temperature for drying with forced air convection is 30° C.

6. A crystalline form CS9 of ARN-509,

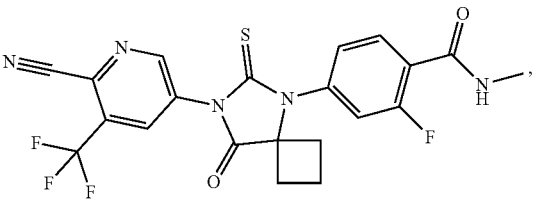 [SMILES: CNC(=O)c1ccc(N2C(=S)N(c3cnc(C#N)c(C(F)(F)F)c3)C(=O)C23CCC3)cc1F]

wherein the X-ray powder diffraction pattern shows characteristic peaks at 2theta values of 7.7±0.2°, 15.0±0.2°, and 18.0±0.2° using CuKα radiation.

7. The crystalline form CS9 according to claim 6, wherein the X-ray powder diffraction pattern shows one or two or three characteristic peaks at 2theta values of 12.3±0.2°, 19.9±0.2° and 20.7±0.2° using CuKα radiation.

8. The crystalline form CS9 according to claim 6, wherein the X-ray powder diffraction pattern shows one or two or three characteristic peaks at 2theta values of 15.5±0.2°, 22.6±0.2° and 23.0±0.2° using CuKα radiation.

9. A process for preparing crystalline form CS9 of ARN-509 according to claim 6, wherein the process comprises:
(1) adding ARN-509 into an nitrile, the mixture of an nitrile and water, the mixture of an nitrile and an alcohol or the mixture of an nitrile and an aromatic hydrocarbon, stirring at 5° C. to 50° C., centrifuging and drying to obtain a solid; or
(2) dissolving ARN-509 into a solvent mixture of methyl acetate, an alcohol and an alkane, heating the solution to 40° C. to 60° C., then cooling to 0° C. to 10° C. to precipitate a solid; or
(3) dissolving ARN-509 into a solvent mixture of acetonitrile and an alcohol, cooling to −20° C. to 5° C. to precipitate a solid.

10. The process for preparing crystalline form CS9 of ARN-509 according to claim 9, wherein in method (1), said nitrile is acetonitrile, said alcohol is methanol or ethanol, said aromatic hydrocarbon is toluene, said stirring temperature is room temperature or 50° C.; in method (2), said alcohol is methanol, said alkane is n-heptane; said heating temperature is 50° C., said cooling temperature is 5° C.; in method (3), said alcohol is isopropanol, said cooling temperature is −20° C.

11. A pharmaceutical composition, wherein said pharmaceutical composition comprises a therapeutically effective amount of crystalline form CS8 according to claim 1, and a pharmaceutically acceptable carrier, a diluent or an excipient.

12. A method of antagonizing an androgen receptor, comprising administering to a subject in need thereof a therapeutically effective amount of crystalline form CS8 according to claim 1.

13. A method of treating prostate cancer, comprising administering to a subject in need thereof a therapeutically effective amount of crystalline form CS8 according to claim 1.

14. The crystalline form CS8 according to claim 2, wherein the X-ray powder diffraction pattern shows one or two or three characteristic peaks at 2theta values of 23.2±0.2°, 16.0±0.2° and 24.0±0.2° using CuKα radiation.

15. The crystalline form CS9 according to claim 7, wherein the X-ray powder diffraction pattern shows one or two or three characteristic peaks at 2theta values of 15.5±0.2°, 22.6±0.2° and 23.0±0.2° using CuKα radiation.

16. A pharmaceutical composition, wherein said pharmaceutical composition comprises a therapeutically effective amount of crystalline form CS9 according to claim 6, and a pharmaceutically acceptable carrier, a diluent or an excipient.

17. A method of antagonizing an androgen receptor, comprising administering to a subject in need thereof a therapeutically effective amount of crystalline form CS9 according to claim 6.

18. A method for treating prostate cancer, comprising administering to a subject in need thereof a therapeutically effective amount of crystalline form CS9 according to claim 6.

* * * * *